(12) United States Patent
Lee

(10) Patent No.: US 7,338,742 B2
(45) Date of Patent: Mar. 4, 2008

(54) PHOTORESIST POLYMER AND PHOTORESIST COMPOSITION CONTAINING THE SAME

(75) Inventor: Geun Su Lee, Gyeonggi-do (KR)

(73) Assignee: Hynix Semiconductor Inc., Kyungki-do (KR)

( * ) Notice: Subject to any disclaimer, the term of this patent is extended or adjusted under 35 U.S.C. 154(b) by 148 days.

(21) Appl. No.: 10/876,029

(22) Filed: Jun. 24, 2004

(65) Prior Publication Data

US 2005/0089800 A1 Apr. 28, 2005

(30) Foreign Application Priority Data

Oct. 8, 2003 (KR) ............... 10-2003-0069898
Dec. 22, 2003 (KR) ............... 10-2003-0094610

(51) Int. Cl.
*G03F 7/039* (2006.01)
*G03F 7/32* (2006.01)

(52) U.S. Cl. ............ 430/270.1; 430/296; 430/326; 526/257; 526/242; 526/243

(58) Field of Classification Search ......... 526/243; 430/326, 296, 325
See application file for complete search history.

(56) References Cited

U.S. PATENT DOCUMENTS

| | | | |
|---|---|---|---|
| 4,138,409 A * | 2/1979 | Wang et al. ............... 549/40 |
| 4,204,007 A * | 5/1980 | Wang et al. ............... 426/548 |
| 4,568,724 A * | 2/1986 | Dean ............... 525/203 |
| 5,212,043 A | 5/1993 | Yamamoto et al. |
| 5,750,680 A | 5/1998 | Kim et al. |
| 5,958,665 A | 9/1999 | Hioki et al. |
| 6,051,678 A | 4/2000 | Kim et al. |
| 6,132,926 A | 10/2000 | Jung et al. |
| 6,143,463 A | 11/2000 | Jung et al. |
| 6,150,069 A | 11/2000 | Jung et al. |
| 6,180,316 B1 | 1/2001 | Kajita et al. |
| 6,225,020 B1 | 5/2001 | Jung et al. |
| 6,235,447 B1 | 5/2001 | Lee et al. |
| 6,235,448 B1 | 5/2001 | Lee et al. |
| 2002/0058207 A1* | 5/2002 | Urano et al. ............... 430/302 |
| 2003/0091933 A1* | 5/2003 | Kunita ............... 430/270.1 |
| 2005/0019638 A1* | 1/2005 | Ravikiran et al. ............ 429/33 |
| 2005/0100826 A1* | 5/2005 | Sato et al. ............... 430/307 |
| 2005/0153233 A1* | 7/2005 | Wu et al. ............... 430/270.1 |
| 2005/0240109 A1 | 10/2005 | Inoue et al. |

FOREIGN PATENT DOCUMENTS

| EP | 0 789 278 A2 | 8/1997 |
|---|---|---|
| EP | 0 794 458 A2 | 9/1997 |
| GB | 2 345 286 A | 7/2000 |
| JP | 8269009 | 10/1996 |
| KR | 10-2005-0014233 A | 2/2005 |
| WO | WO96/37526 | 11/1996 |
| WO | WO97/33198 | 9/1997 |

OTHER PUBLICATIONS

Kaz'mina et al, AN 1979:137784, CAPLUS from ACS on STN, English abstract entered May 12, 1984, of "Reaction of hexafuorobutadiene with sulfur trioxide", izvestiya Akademii Nauk SSSR, seriya Kimicheskay (1979), vol. 1, pp. 118-126.*

Tamaur et al "Palladium-Catalyzed [2,3] Rearrangement of Alkyl Allyl Sulfites to Alkyl Allylsulfonates", J. Org. Chem, 1990, 55, 1823-1829.*

Smith et al, "Lithium Aluminum Hydride-Aluminum Hydride Reduction of Sultones", J. Org. Chem, vol. 46, 1981, pp. 101-106.*

* cited by examiner

*Primary Examiner*—Cynthia Hamilton
(74) *Attorney, Agent, or Firm*—Marshall, Gerstein & Borun LLP

(57) ABSTRACT

The present invention relates to photoresist polymers and photoresist compositions. The disclosed photoresist polymers and photoresist compositions containing the same have excellent transmittance, etching resistance, thermal resistance and adhesive property, low light absorbance and high affinity to a developing solution at a wavelength of 193 nm and 157 nm, thereby improving LER (line edge roughness).

43 Claims, 10 Drawing Sheets

PHOTORESIST POLYMER AND PHOTORESIST COMPOSITION CONTAINING THE SAME

BACKGROUND

1. Technical Field

The present invention relates to photoresist polymers and photoresist compositions comprising the same. More specifically, it relates to compounds represented by Formula 1 described herein as photoresist monomers, photoresist polymers containing the same, and photoresist compositions that have excellent transmittance, etching resistance, thermal resistance, adhesive property, and low light absorbance at a wavelength of 13 nanomometers (nm) as well as 193 nm and 157 nm and high affinity to a developing solution, thereby improving line edge roughness (hereinafter, referred to as "LER").

2. Description of the Related Art

In order to be used as photoresists for ArF and VUV (vacuum ultraviolet), photoresist polymers and photoresist compositions are required to have low light absorbance at wavelengths of 193 nm and 157 nm, excellent etching resistance and adhesive property on the substrate, and to be developed with 2.38 wt % and 2.6 wt % TMAH solution. Recently, much research has been focused to develop resins having high transparency at 248 nm and 193 nm wavelengths and etching resistance similar to novolac resin.

However, since the thickness of photoresist materials becomes thinner as circuits of semiconductor devices become more microfine, it is difficult to improve the LER of the patterns. Conventional photoresist materials have also strong light absorbance at a wavelength of 157 nm, thus they are improper for use at 157 nm wavelength.

The LER occurs more frequently in ArF photoresist patterns than in conventional KrF or I-line photoresist patterns. The conventional KrF or I-line photoresist materials include acidic alcohol groups while most ArF photoresist materials include no acidic alcohol group. As a result, since the ArF photoresist materials have low affinity to basic development solutions, the LER occurs more severely when using ArF photoresist materials.

In order to solve the above-described problems, polyethylene and polyacrylate resins comprising fluorine have been used. However, such polyethylene and polyacrylate resins comprising fluorine have low etching resistance and decreased adhesive properties to a silicon substrate.

Furthermore, the polyethylene and polyacrylate resins are not suitable to be used commercially because they are expensive and their mass-production is difficult. Moreover, the protecting group of the conventional photoresist polymer is destroyed in the baking process after exposure and generates gases when patterns are formed using chemically-amplified photoresists, resulting in the damage of the lens.

This phenomenon occurs inevitably when patterns are formed using chemically amplified photoresists, and decreased stability of the subsequent processes results in the reduction of the yield of the semiconductor devices.

SUMMARY OF THE DISCLOSURE

Disclosed herein are photoresist polymers that have excellent transmittance, etching resistance, thermal resistance and adhesive property, low light absorbance and high affinity to an developing solution, thereby obtaining patterns with improved LER.

A suitable photoresist monomer is shown in Formula 1, below:

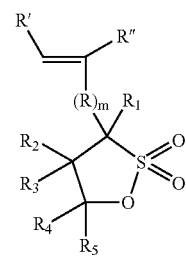

[Formula 1]

wherein
R is $CH_2$, $CHCH_2$, or $C(CH_2)_2$;
R' and R'' are individually H or $CH_3$;
$R_1$, $R_2$, $R_3$, $R_4$, and $R_5$ are individually H, F, $C_1$–$C_{20}$ alkyl, $C_1$–$C_{20}$ perfluoroalkyl, $C_1$–$C_{20}$ alkyl comprising an ether group (—O—), $C_1$–$C_{20}$ perfluoroalkyl comprising an ether group (—O—), $C_1$–$C_{20}$ alkyl partially substituted with F, or $C_1$–$C_{20}$ alkyl comprising an ether group and partially substituted with F; and,
m is an integer ranging from 0 to 3.

A suitable photoresist polymer includes a repeating unit as shown in FIG. 2

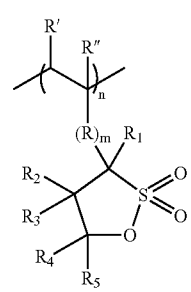

[Formula 2]

wherein
R is $CH_2$, $CHCH_2$, or $C(CH_2)_2$;
R' and R'' are individually H or $CH_3$;
$R_1$, $R_2$, $R_3$, $R_4$, and $R_5$ are individually H, F, $C_1$–$C_{20}$ alkyl, $C_1$–$C_{20}$ perfluoroalkyl, $C_1$–$C_{20}$ alkyl comprising an ether group (—O—), $C_1$–$C_{20}$ perfluoroalkyl comprising an ether group (—O—), $C_1$–$C_{20}$ alkyl partially substituted with F, or $C_1$–$C_{20}$ alkyl comprising an ether group and partially substituted with F; and,
m is an integer ranging from 0 to 3, and n is an integer ranging from 10 to 150.

Also disclosed herein are photoresist compositions comprising above photoresist polymers and a method for forming photoresist patterns using said compositions.

DETAILED DESCRIPTION OF THE PRESENTLY PREFERRED EMBODIMENTS

Figure 1:
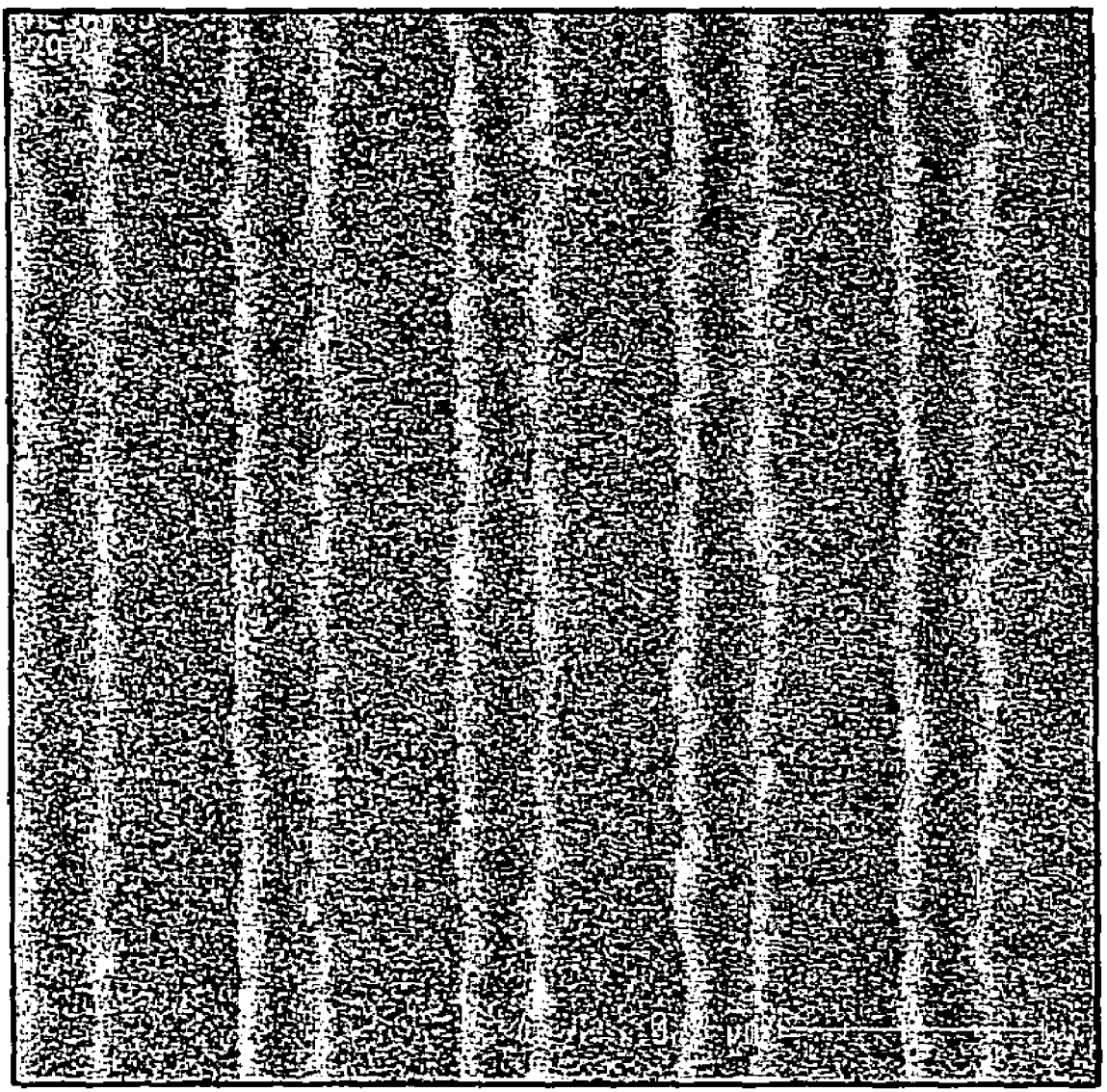
FIG. 1 is a photograph illustrating a photoresist pattern obtained from Example 17.

The present invention provides sultone compounds used as photoresist monomers, photoresist polymers comprising said sultone compounds and photoresist compositions comprising the same.

The sultone compound used as a photoresist monomer is represented by the following Formula 1:

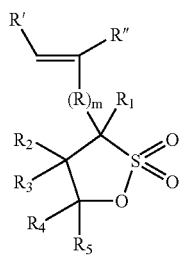

[Formula 1]

wherein

R is $CH_2$, $CHCH_2$, or $C(CH_2)_2$;

R' and R" are individually H or $CH_3$;

$R_1$, $R_2$, $R_3$, $R_4$, and $R_5$ are individually H, F, $C_1$–$C_{20}$ alkyl, $C_1$–$C_{20}$ perfluoroalkyl, $C_1$–$C_{20}$ alkyl comprising an ether group (—O—), $C_1$–$C_{20}$ perfluoroalkyl comprising an ether group (—O—), $C_1$–$C_{20}$ alkyl partially substituted with F, or $C_1$–$C_{20}$ alkyl comprising ether group and partially substituted with F; and, m is an integer ranging from 0 to 3.

Here, the compound represented by Formula 1 may be synthesized by the methods disclosed in Tetrahedron, Vol. 33, pp. 1113–1118 (1977), and J. Am. Chem. Soc, 82, 6181 (1960).

Preferably, the compound of Formula 1 used as the photoresist monomer in the present invention is selected from the group consisting of Formulas 1a to 1f, where m is 0.

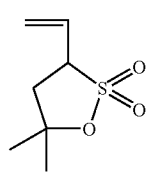

[Formula 1a]

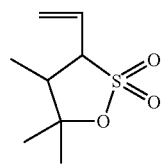

[Formula 1b]

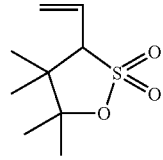

[Formula 1c]

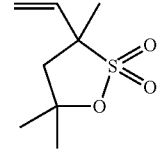

[Formula 1d]

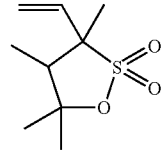

[Formula 1e]

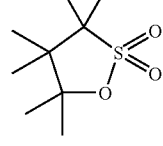

[Formula 1f]

Preferably, the compound of Formula 1 is selected from the group consisting of Formulas 1g to 1L where R is $CH_2$ and m is 1.

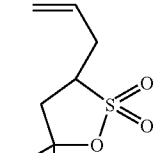

[Formula 1g]

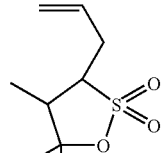

[Formula 1h]

[Formula 1i]

-continued

[Formula 1j]

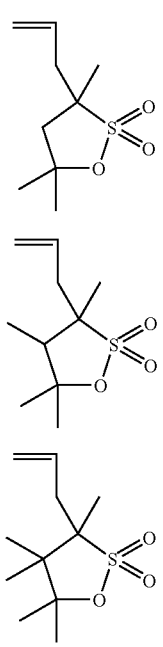

[Formula 1k]

[Formula 1L]

Also, the present invention provides a photoresist polymer comprising a repeating unit represented by Formula 2.

[Formula 2]

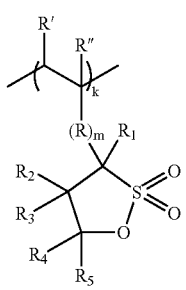

wherein

R is $CH_2$, $CHCH_3$, or $C(CH_3)_2$;

R' and R" are individually H or $CH_3$;

$R_1$, $R_2$, $R_3$, $R_4$, and $R_5$ are individually H, F, $C_1$–$C_{20}$ alkyl, $C_1$–$C_{20}$ perfluoroalkyl, $C_1$–$C_{20}$ alkyl comprising an ether group (—O—), $C_1$–$C_{20}$ perfluoroalkyl comprising an ether group (—O—), $C_1$–$C_{20}$ alkyl partially substituted with F, or $C_1$–$C_{20}$ alkyl comprising ether group and partially substituted with F; and, m is an integer ranging from 0 to 3, and k is an integer ranging from 10 to 150.

Since the photoresist polymer of the present invention comprises a sultone group, the polymer has high adhesive property to a silicon substrate and low absorbance at a wavelength of 193 nm and 157 nm. In the baking process, acid produced by the exposure to light causes a reaction represented by Reaction 1 (shown below). Accordingly, a degassing reaction, which is a problem of the conventional chemical amplification photoresist, does not occur, thereby preventing damage to the lens. Moreover, a product from the exposed area which includes sulfonic acid produced by the above reaction is easily dissolved in a developing solvent, thereby improving the LER of the patterns.

[Reaction 1]

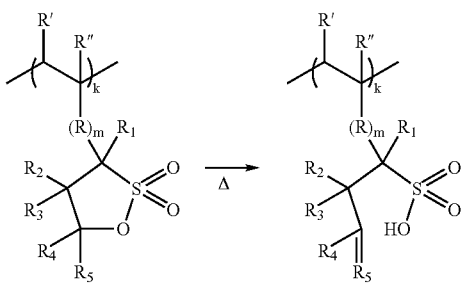

The repeating unit of Formula 2 is preferably selected from the group consisting of Formulas 2a to 2L:

[Formula 2a]

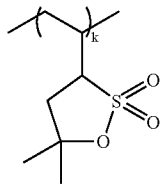

[Formula 2b]

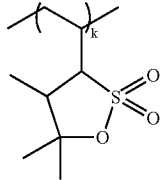

[Formula 2c]

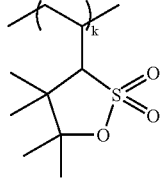

[Formula 2d]

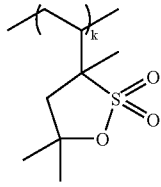

[Formula 2e]

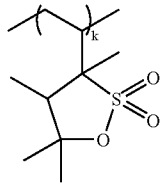

[Formula 2f]

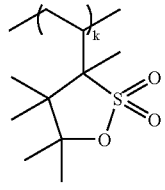

-continued

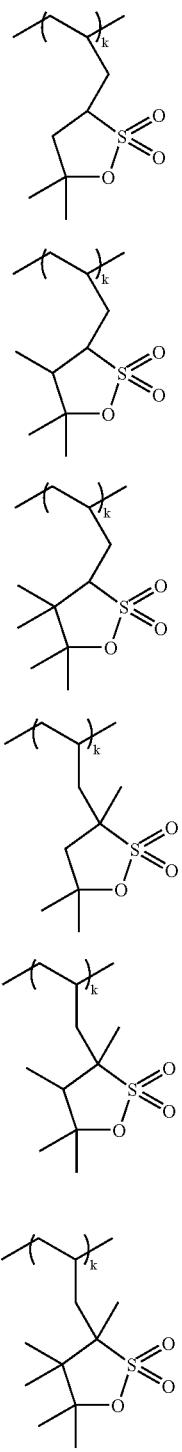

[Formula 2g]

[Formula 2h]

[Formula 2i]

[Formula 2j]

[Formula 2k]

[Formula 2L]

In the formulas 2a through 2L, k is an integer ranging from 10 to 150.

In addition, the present invention provides a method for forming the polymer of Formula 2 comprising the steps of:
R is $CH_2$, $CHCH_3$, or $C(CH_3)_2$;
R''' is $C_1$–$C_5$ alkylene; presence of a salt to obtain the compound of Formula 1; and, (b) polymerizing the compound of Formula 1 in the presence of a polymerization initiator.

[Formula 3]

[Formula 4]

wherein
R is $CH_2$, $CHCH_2$, or $C(CH_2)_2$;
R' and R" are individually H or $CH_3$;
$R_1$, $R_2$, $R_3$, $R_4$, and $R_5$ are individually H, F, $C_1$–$C_{20}$ alkyl, $C_1$–$C_{20}$ perfluoroalkyl, $C_1$–$C_{20}$ alkyl comprising an ether group (—O—), $C_1$–$C_{20}$ perfluoroalkyl comprising an ether group (—O—), $C_1$–$C_{20}$ alkyl partially substituted with F, or $C_1$–$C_{20}$ alkyl comprising an ether group and partially substituted with F;
X is F, Cl, or Br; and,
m is an integer ranging from 0 to 3.

The polymerization reaction is a radical polymerization reaction performed by means of bulk polymerization or solution polymerization. As disclosed in WO 96/37526 (Nov. 28, 1996), the polymerization may be performed using a metal catalyst.

Preferably, the salt used in the step (a) is selected from the group consisting of NaH, n-BuLi, Lithium diiopropylamine (LDA), and LiH.

Preferably, the polymerization solvent of the step (b) is selected from the group consisting of cyclohexanone, cyclopentanone, tetrahydrofuran, dimethylformamide, dimethylsulfoxide, dioxane, methylethylketone, benzene, toluene, xylene, and mixtures thereof.

Additionally, the polymerization initiator used in the step (b) is preferably selected from the group consisting of benzoyl peroxide, 2,2'-azobisisobutyronitrile (AIBN), acetylperoxide, laurylperoxide, t-butylperacetate, t-butylhydroperoxide, and di-t-butylperoxide.

The polymer formed by the above-described method is preferably crystallized and purified by using the solvent selected from the group consisting of dimethylether, petroleum ether, lower alcohol such as methanol, ethanol, and iso-propanol, water, and mixtures thereof.

The photoresist polymer of the present invention comprises a repeating unit represented by Formula 5:

[Formula 5]

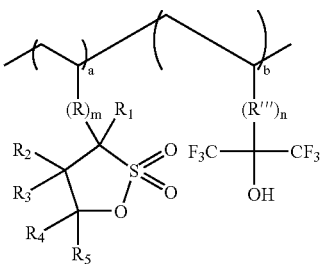

wherein

R is $CH_2$, $CHCH_3$, or $C(CH_3)_2$;

R''' is $C_1$–$C_5$ alkylene;

$R_1$, $R_2$, $R_3$, $R_4$, and $R_5$ are individually H, F, $C_1$–$C_{20}$ alkyl, $C_1$–$C_{20}$ perfluoroalkyl, $C_1$–$C_{20}$ alkyl comprising an ether group (—O—), $C_1$–$C_{20}$ perfluoroalkyl comprising an ether group (—O—), $C_1$–$C_{20}$ alkyl partially substituted with F, or $C_1$–$C_{20}$ alkyl comprising an ether group and partially substituted with F, with the proviso that if $R_1$, $R_2$, and $R_3$ are all H, then $R_4$ and $R_5$ are different from H;

n and m individually are an integer ranging from 0 to 3; and, the relative ratio of a:b=15–99.9 mol %:0.1–85 mol %, preferably 20–90 mol % :10–80 mol %.

Preferably, the repeating unit of Formula 5 is selected from the group consisting of Formulas 5a to 5x:

[Formula 5a]

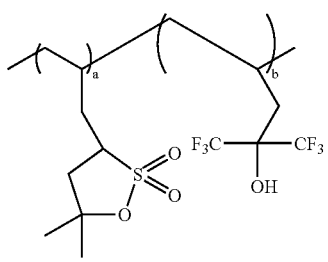

[Formula 5b]

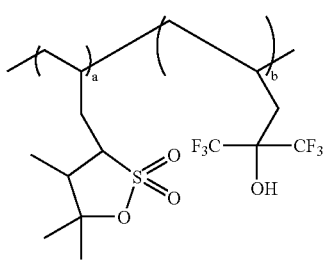

[Formula 5c]

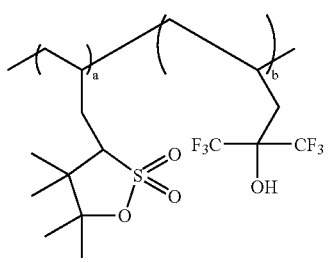

[Formula 5d]

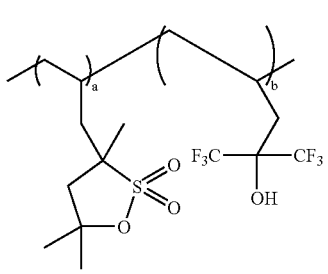

-continued

[Formula 5e]

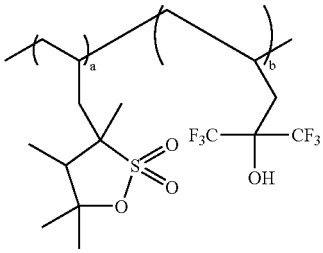

[Formula 5f]

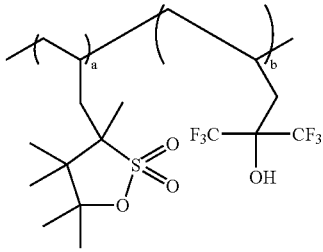

[Formula 5g]

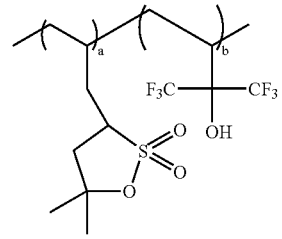

[Formula 5h]

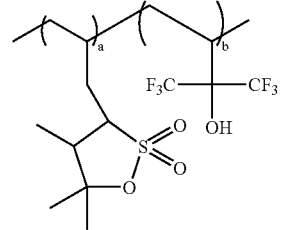

[Formula 5i]

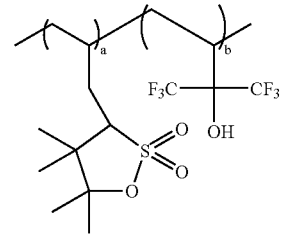

[Formula 5j]

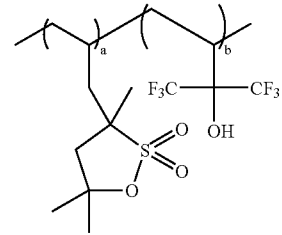

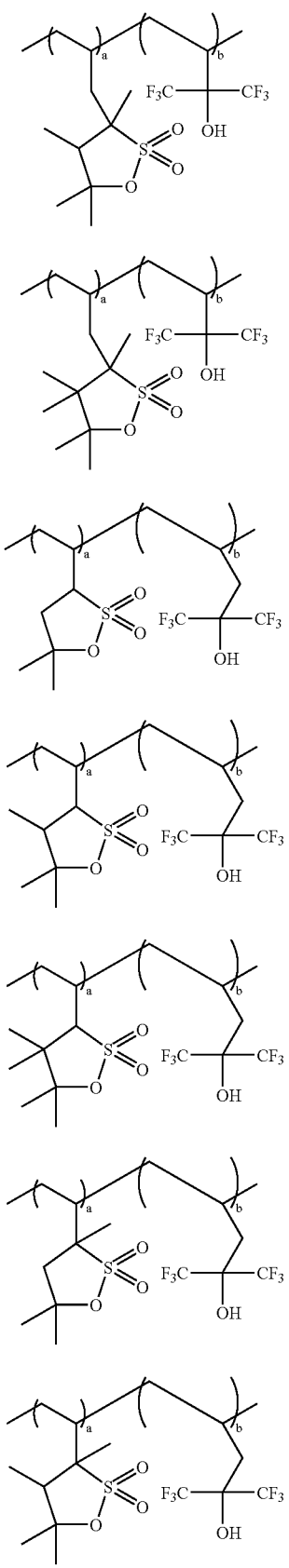
[Formula 5k]
[Formula 5L]
[Formula 5m]
[Formula 5n]
[Formula 5o]
[Formula 5p]
[Formula 5q]
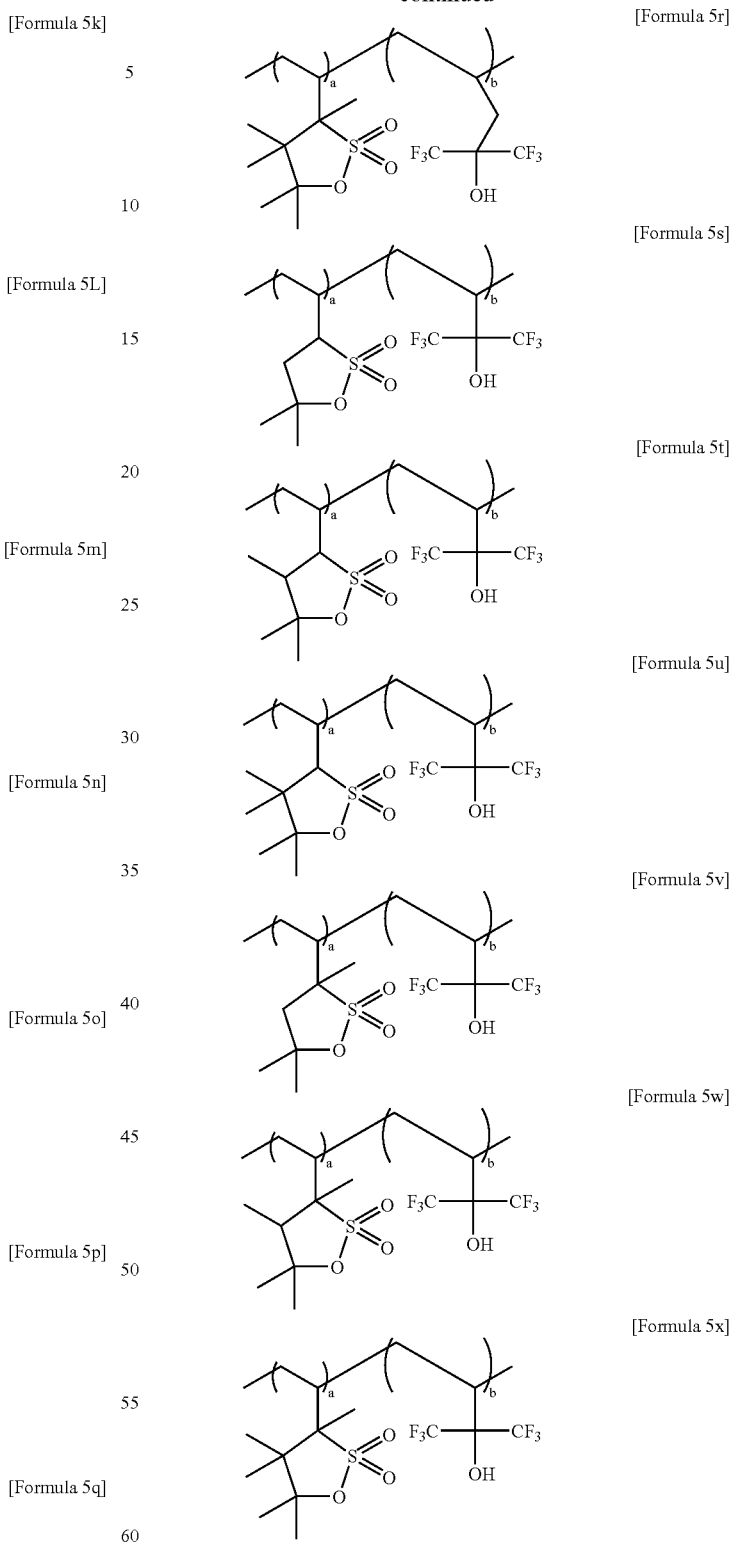
[Formula 5r]
[Formula 5s]
[Formula 5t]
[Formula 5u]
[Formula 5v]
[Formula 5w]
[Formula 5x]
In the Formulas 5a to 5x, the relative ratio of a:b=15–99.9 mol %:0.1–85 mol %.
The repeating unit of Formula 5 is present in a molar ratio of 10–95 mol %:90–5 mol %, preferably 20–80 mol %:80–20 mol % relative to total molar percent of the polymer.

Preferably, the polymer represented by Formula 5 comprises a first repeating unit represented by Formula 6a and a second repeating unit represented by Formula 6b.

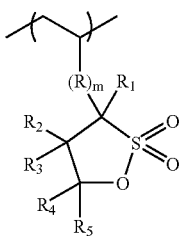

[Formula 6a]

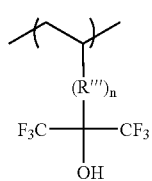

[Formula 6b]

The polymers of the present invention comprise acidic alcohol groups having high affinity to basic developing solutions. In addition, since the polymers of the present invention comprise fluorine atoms, the occurrence of high light absorbance at 157 nm wavelength observed in the conventional hybrid-type photoresist may be decreased.

Since the photoresist polymer of the present invention comprises a sultone group, the polymer has high adhesive property to a silicon substrate and low absorbance at a wavelength of 193 nm and 157 nm. In the baking step, acid produced by exposure to light causes the reaction represented by Reaction 2. A degassing reaction, which is a problem of the conventional chemical amplification photoresist, does not occur, thereby preventing damage to the lens.

[Reaction 2]

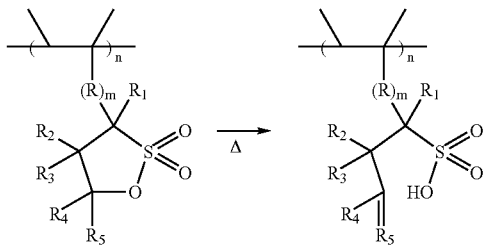

In addition, the present invention provides a method for forming the polymer of Formula 5 comprising the steps of:

(a) reacting compounds of Formulas 7 and 8 in the presence of a salt to obtain a compound of Formula 9; and, (b) polymerizing compounds of Formulas 9 and 10 in the presence of a polymerization initiator:

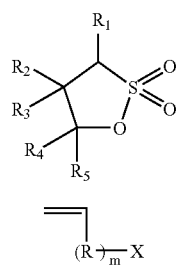

[Formula 7]

[Formula 8]

-continued

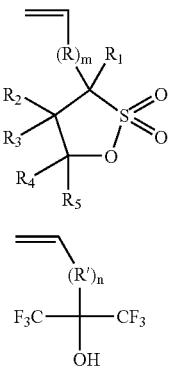

[Formula 9]

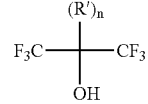

[Formula 10]

wherein

R and R' are individually $C_1$–$C_5$ alkyl;

$R_1$, $R_2$, $R_3$, $R_4$, and $R_5$ are individually H, F, $C_1$–$C_{20}$ alkyl, $C_1$–$C_{20}$ perfluoroalkyl, $C_1$–$C_{20}$ alkyl comprising an ether group (—O—), $C_1$–$C_{20}$ perfluoroalkyl comprising an ether group (—O—), $C_1$–$C_{20}$ alkyl partially substituted with F, or $C_1$–$C_{20}$ alkyl comprising ether group and partially substituted with F;

X is F, Cl, or Br; and, n and m are individually an integer ranging from 0 to 3.

The polymerization reaction is a radical polymerization reaction performed by means of bulk polymerization or solution polymerization. As disclosed in WO 96/37526 (Nov. 28, 1996), the polymerization may be performed using a metal catalyst.

Preferably, the salt of the step (a) is selected from the group consisting of NaH, n-BuLi, Lithium diiopropylamine (LDA), and LiH.

Preferably, the polymerization solvent of the step (b) is selected from the group consisting of cyclohexanone, cyclopentanone, tetrahydrofuran, dimethylformamide, dimethylsulfoxide, dioxane, methylethylketone, benzene, toluene, xylene, and mixtures thereof.

Additionally, the polymerization initiator of the step (b) is preferably selected from the group consisting of benzoyl peroxide, 2,2'-azobisisobutyronitrile (AIBN), acetylperoxide, laurylperoxide, t-butylperacetate, t-butylhydroperoxide, and di-t-butylperoxide.

The polymer formed by the above-described method is preferably crystallized and purified using solution selected from the group consisting of dimethylether, petroleum ether, lower alcohol such as methanol, ethanol, and iso-propanol, water, and mixtures thereof.

Furthermore, the present invention provides a photoresist composition comprising the above-described photoresist polymer, a photoacid generator, and an organic solvent. The composition may further comprise a vinylene or acryl based polymer.

Any of the conventional photoacid generators, which are able to produce acids when they are exposed to light, can be used in the photoresist composition of the present invention. Some of the conventional photoacid generators are disclosed in U.S. Pat. No. 5,212,043 (May 18, 1993), WO 97/33198 (Sep. 12, 1997), WO 96/37526 (Nov. 28, 1996), EP 0 794 458 (Sep. 10, 1997), EP 0 789 278 (Aug. 13, 1997), U.S. Pat. No. 5,750,680 (May 12, 1998), U.S. Pat. No. 6,051,678 (Apr. 18, 2000), GB 2,345,286 A (Jul. 5, 2000), U.S. Pat. No. 6,132,926 (Oct. 17, 2000), U.S. Pat. No. 6,143,463 (Nov. 7, 2000), U.S. Pat. No. 6,150,069 (Nov. 21, 2000), U.S. Pat.

No. 6,180,316 B1 (Jan. 30, 2001), U.S. Pat. No. 6,225,020 B1 (May 1, 2001), U.S. Pat. No. 6,235,448 B1 (May 22, 2001), and U.S. Pat. No. 6,235,447 B1 (May 22, 2001). Sulfide type or onium type compounds are mostly used for the photoacid generator.

More preferably, the photoacid generator is selected from the group consisting of phthalimidotrifluoromethane sulfonate, dinitrobenzyl-tosylate, n-decyl disulfone, and naphthylimido trifluoromethane sulfonate having low absorbance at 157 nm and 193 nm. Also, the photoacid generator may be further selected from the group consisting of diphenyl iodide hexafluorophosphate, diphenyl iodide hexafluoroarsenate, diphenyl iodide hexafluoroantimonate, diphenyl p-methoxyphenylsulfonium triflate, diphenyl p-toluenylsulfonium triflate, diphenyl p-isobutylphenyl-sulfonium triflate, triphenylsulfonium hexafluoroarsenate, triphenylsulfonium hexafluoroantimonate, triphenyl-sulfonium triflate, and dibutyl-naphthylsulfonium triflate. The photoacid generator is preferably present in an amount ranging from 0.05 weight percent (wt %) to 10 wt % based upon total weight of the photoresist polymer. If the photoresist generator is present in the amount of less than 0.05 wt %, it lowers photosensitivity of the photoresist composition. If the photoacid generator is present in the amount of more than 10 wt %, it results in the formation of a pattern with poor profile due to its high absorption of far ultraviolet rays and excessively generated acid.

Any of the organic solvents can be used, including some of conventional organic solvents disclosed in U.S. Pat. No. 5,212,043 (May 18, 1993), WO 97/33198 (Sep. 12, 1997), WO 96/37526 (Nov. 28, 1996), EP 0 794 458 (Sep. 10, 1997), EP 0 789 278 (Aug. 13, 1997), U.S. Pat. No. 5,750,680 (May 12, 1998), U.S. Pat. No. 6,051,678 (Apr. 18, 2000), GB 2,345,286 A (Jul. 5, 2000), U.S. Pat. No. 6,132, 926. (Oct. 17, 2000), U.S. Pat. No. 6,143,463 (Nov. 7, 2000), U.S. Pat. No. 6,150,069 (Nov. 21, 2000), U.S. Pat. No. 6,180,316 B1 (Jan. 30, 2001), U.S. Pat. No. 6,225,020 B1 (May 1, 2001), U.S. Pat. No. 6,235,448 B1 (May 22, 2001), and U.S. Pat. No. 6,235,447 B1 (May 22, 2001). Preferably, the organic solvent is selected from the group consisting of diethylene glycol diethyl ether, methyl 3-methoxypropionate, ethyl 3-ethoxypropionate, propylene glycol methyl ether acetate, cyclohexanone, 2-heptanone, and ethyl lactate. The organic solvent is present in an amount ranging from 500 wt % to 2000 wt % based on the weight of the photoresist polymer in order to obtain a desired thickness of the photoresist film. For example, the thickness of the photoresist film is about 0.25 micrometers (μm) when the organic solvent is present in the amount of about 1000 wt % based upon total weight of the photoresist polymer.

In addition, the present invention provides a method for forming a photoresist pattern comprising the steps of:

(a) coating the above-described photoresist composition on the top portion of an underlying layer to be etched to form a photoresist film;

(b) exposing the photoresist film to light;

(c) baking the exposed photoresist film; and, (d) developing the photoresist film to obtain a photoresist pattern.

The above method may further comprise additional baking step before the exposing step (b). Here, the baking step is performed at a temperature ranging from 70° C. to 200° C.

The exposing step is performed using a light source selected from the group consisting of KrF, ArF, ETV (Extreme Ultra Violet), VUV (Vacuum Ultra Violet), E-beam, X-ray, and ion beam as well as Ar with exposing energy ranging from 0.1 millijoules per square centimeter (mJ/cm$^2$) to 100 (mJ/cm$^2$).

The developing step (d) is preferably performed using an alkaline developing solution such as a TMAH aqueous solution in an amount ranging from 0.01 wt % to 5 wt %.

In addition, the present invention provides a semiconductor device manufactured by the patterning method described above.

The photoresist polymers and photoresist compositions of the present invention will be described in more detail referring to the following non-limiting examples.

I. Preparation of Photoresist Polymer

EXAMPLE 1

Synthesis of Compound of Formula 1b 0.1M of 2,3,3-trimethyl-1,3-propane sultone was dissolved in tetrahydrofuran anhydride under a nitrogen atmosphere, and 0.1M of NaH was added thereto. The prepared solution was stirred for 10 minutes, and then 0.11M of vinyl bromide was added thereto. The obtained mixture was further reacted at room temperature for 3 hours. After the reaction was completed, the reacted mixture was filtered to remove NaBr. Then, by precipitation of the resulting material in a diethylether/pentane mixed solution, the compound of Formula 1b was obtained (yield: 92%).

EXAMPLE 2

Synthesis of Compound of Formula1c

The same procedure of Example 1 was performed using 2,2,3,3-tetramethyl-1,3-propane sultone instead of 2,3,3-trimethyl-1,3-propane sultone, and obtained the compound of Formula1c (yield: 96%).

EXAMPLE 3

Synthesis of Compound of Formula 1e

The same procedure of Example 1 was performed using 1,2,3,3-tetramethyl-1,3-propane sultone instead of 2,3,3-trimethyl-1,3-propane sultone, and obtained the compound of Formula 1e (yield: 92%).

EXAMPLE 4

Synthesis of Compound of Formula 1h

The same procedure of Example 1 was performed using allyl bromide instead of vinyl bromide, and obtained the compound of Formula 1h (yield: 86%).

EXAMPLE 5

Synthesis of Compound of Formula 1i

The same procedure of Example 2 was performed using allyl bromide instead of vinyl bromide, and obtained the compound of Formula 1i (yield: 89%).

EXAMPLE 6

Synthesis of Compound of Formula 1k

The same procedure of Example 3 was performed using allyl bromide instead of vinyl bromide, and obtained the compound of Formula 1i (yield: 87%).

II. Preparation of Photoresist Polymer

EXAMPLE 7

Synthesis of Compound of Formula 2b

To 30 mL of tetrahydrofuran were added 0.05M of the compound of Formula 1b obtained from Example 1 and 0.20 g of AIBN. The prepared mixture was reacted at 65° C. for 6 hours. After the reaction was complete, hexane was added to the resulting mixture to make it into a solid state. Then, the solid was lyophilized, thereby obtaining the polymer of Formula 2b (yield: 53%).

EXAMPLE 8

Synthesis of Compound of Formula 2c

To 30 mL of tetrahydrofuran were added 0.05M of the compound of Formula 1c obtained from Example 2 and 0.20 g of AIBN. The prepared mixture was reacted at 65° C. for 6 hours. After the reaction was complete, hexane was added to the resulting mixture to make it into a solid state. Then, the solid was lyophilized, thereby obtaining the polymer of Formula 2c (yield: 52%).

EXAMPLE 9

Synthesis of Compound of Formula 2e

To 30 mL of tetrahydrofuran were added 0.05M of the compound of Formula 1e obtained from Example 3 and 0.20 g of AIBN. The prepared mixture was reacted at 65° C. for 6 hours. After the reaction was complete, hexane was added to the resulting mixture to make it into a solid state. Then, the solid was lyophilized, thereby obtaining the polymer of Formula 2e (yield: 53%).

EXAMPLE 10

Synthesis of Compound of Formula 2h

To 30 mL of tetrahydrofuran were added 0.05M of the compound of Formula 1h obtained from Example 4 and 0.20 g of AIBN. The prepared mixture was reacted at 65° C. for 6 hours. After the reaction was complete, hexane was added to the resulting mixture to make it into a solid state. Then, the solid was lyophilized, thereby obtaining the polymer of Formula 2h (yield: 50%).

EXAMPLE 11

Synthesis of Compound of Formula 2i

To 30 mL of tetrahydrofuran were added 0.05M of the compound of Formula 1i obtained from Example 5 and 0.20 g of AIBN. The prepared mixture was reacted at 65°C. for 6 hours. After the reaction was complete, hexane was added to the resulting mixture to make it into a solid state. Then, the solid was lyophilized, thereby obtaining the polymer of Formula 2i (yield: 50%).

EXAMPLE 12

Synthesis of Compound of Formula 2k

To 30 mL of tetrahydrofuran were added 0.05M of the compound of Formula 1k obtained from Example 6 and 0.20 g of AIBN. The prepared mixture was reacted at 65° C. for 6 hours. After the reaction was complete, hexane was added to the resulting mixture to make it into a solid state. Then, the solid was lyophilized, thereby obtaining the polymer of Formula 2k (yield: 50%).

EXAMPLE 13

Synthesis of Compound of Formula 5b (Step 1)
0.1M of 2,3,3-trimethyl-1,3-propane sultone was dissolved in tetrahydrofuran anhydride under a nitrogen atmosphere, and 0.1M of NaH was added thereto. The prepared mixture was stirred for 10 minutes, and then 0.11M of allyl bromide was added thereto. The obtained mixture was further reacted at room temperature for 3 hours. After the reaction was completed, the reacted mixture was filtered to remove NaBr. By crystallization of the resulting material in a diethylether/pentane, 2-(1-prepene-3-yl)-3,4,4-trimethyl sultone was obtained in a pure state (yield: 87%).

(Step 2)
To 30 mL of tetrahydrofuran were added 0.01M of 2-(1-prepene-3-yl)-3,4,4-trimethyl sultone obtained from the step 1, 0.05M of 4-hydroxy-4,4,-di(trifluoromethyl)butane and 0.20 g of AIBN. The prepared mixture was reacted at 65° C. for 6 hours. After the reaction was complete, hexane was added to the resulting mixture to make it into a solid state. Then, the solid was lyophilized, thereby obtaining the polymer of Formula 5b (yield: 49%).

EXAMPLE 14

Synthesis of Compound of Formula 5h

To 30 mL of tetrahydrofuran were added 0.01M of 2-(1-prepene-3-yl)-3,4,4-trimethyl sultone obtained from the step 1 of the Example 13, 0.05M of 3-hydroxy-3,3,-di(trifluoromethyl)propene and 0.20 g of AIBN. The prepared mixture was reacted at 65° C. for 6 hours. After the reaction was complete, hexane was added to the resulting mixture to make it into a solid state. Then, the solid was lyophilized, thereby obtaining the polymer of Formula 5h (yield: 50%).

EXAMPLE 15

Synthesis of Compound of Formula 5c (Step 1)
0.1M of 2,2,3,3-tetramethyl-1,3-propane sultone was dissolved in tetrahydrofuran anhydride under a nitrogen atmosphere, and 0.1M of NaH was added thereto. The prepared mixture was stirred for 10 minutes, and then 0.11M of allyl bromide was added thereto. The obtained mixture was further reacted at room temperature for 3 hours. After the reaction was completed, the resulting mixture was filtered to remove NaBr. By crystallization of the resulting material in a diethylether/pentane, 2-(1-prepene-3-yl)-3,3,4,4-tetramethyl sultone was obtained in pure state (yield: 87%).

(Step 2)
To 30 mL of tetrahydrofuran were added 0.01M of 2-(1-prepene-3-yl)-3,3,4,4-tetramethyl sultone obtained from the step 1, 0.05M of 4-hydroxy-4,4,-di(trifluoromethyl)butane and 0.20 g of AIBN. The prepared mixture was reacted at 65° C. for 6 hours. After the reaction was complete, hexane was added to the resulting mixture to make it into a solid state. Then, the solid was lyophilized, thereby obtaining the polymer of Formula 5c (yield: 49%).

EXAMPLE 16

Synthesis of Compound of Formula 5i

To 30 mL of tetrahydrofuran were added 0.01M of 2-(1-prepene-3-yl)-3,3,4,4-trimethyl sultone obtained from the step 1 of the Example 15, 0.05M of 3-hydroxy-3,3,-di (trifluoromethyl)propene and 0.20 g of AIBN. The prepared mixture was reacted at 65° C. for 6 hours. After the reaction was complete, hexane was added to the resulting mixture to make it into a solid state. Then, the solid was lyophilized, thereby obtaining the polymer of Formula 5i (yield: 49%).

III. Preparation of Photoresist Compositions and Formation of Photoresist Patterns

EXAMPLE 17

To 30 g of propyleneglycolmethyl ether acetate (PGMEA) were added 2 g of the polymer obtained from Example 7, 0.024 g of phthalimidotrifluoromethane sulfonate and 0.06 g of triphenylsulfonium triflate both of which are photoacid generators. The resulting mixture was filtered with a 0.20 µm filter, thereby obtaining a photoresist composition of the present invention.

The photoresist composition was spin-coated on a silicon wafer to form a photoresist film, and soft-baked in oven or hot plate at 130° C. for 90 seconds. After baking, the photoresist film was exposed to light using an ArF laser exposer, and then post-baked at 130° C. for 90 seconds. The baked wafer was developed in a 2.38 wt % TMAH aqueous solution for 40 seconds to obtain 0.08 µm of L/S pattern (see FIG. 1).

EXAMPLE 18

Figure 2:
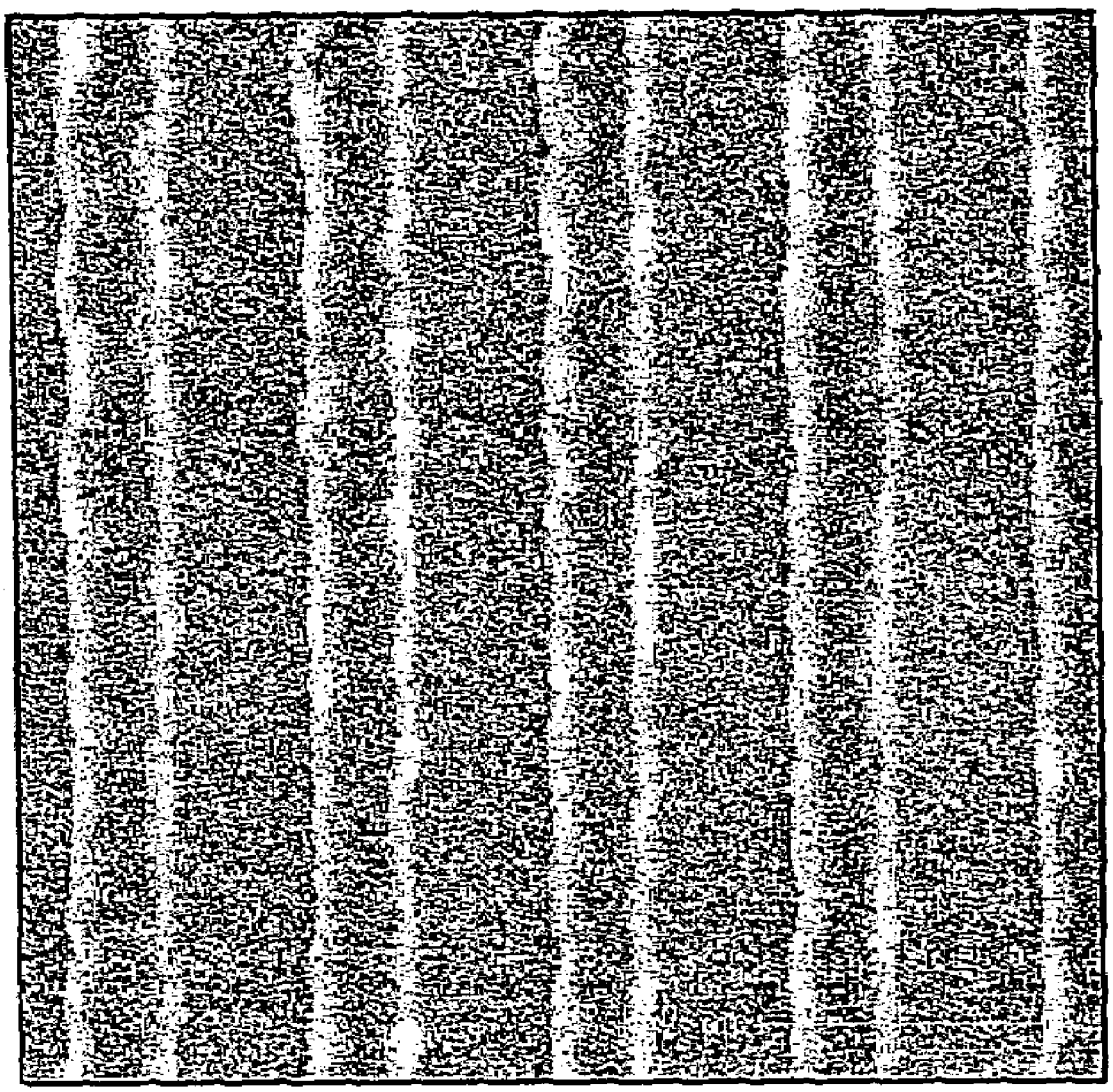
FIG. 2 is a photograph illustrating a photoresist pattern obtained from Example 18.

Photoresist composition was prepared using the same procedure of Example 17 except that 2 g of the polymer obtained from Example 8 was used instead of the polymer obtained from Example 7, and 0.08 µm of L/S pattern was obtained using said photoresist composition (see FIG. 2).

EXAMPLE 19

Figure 3:
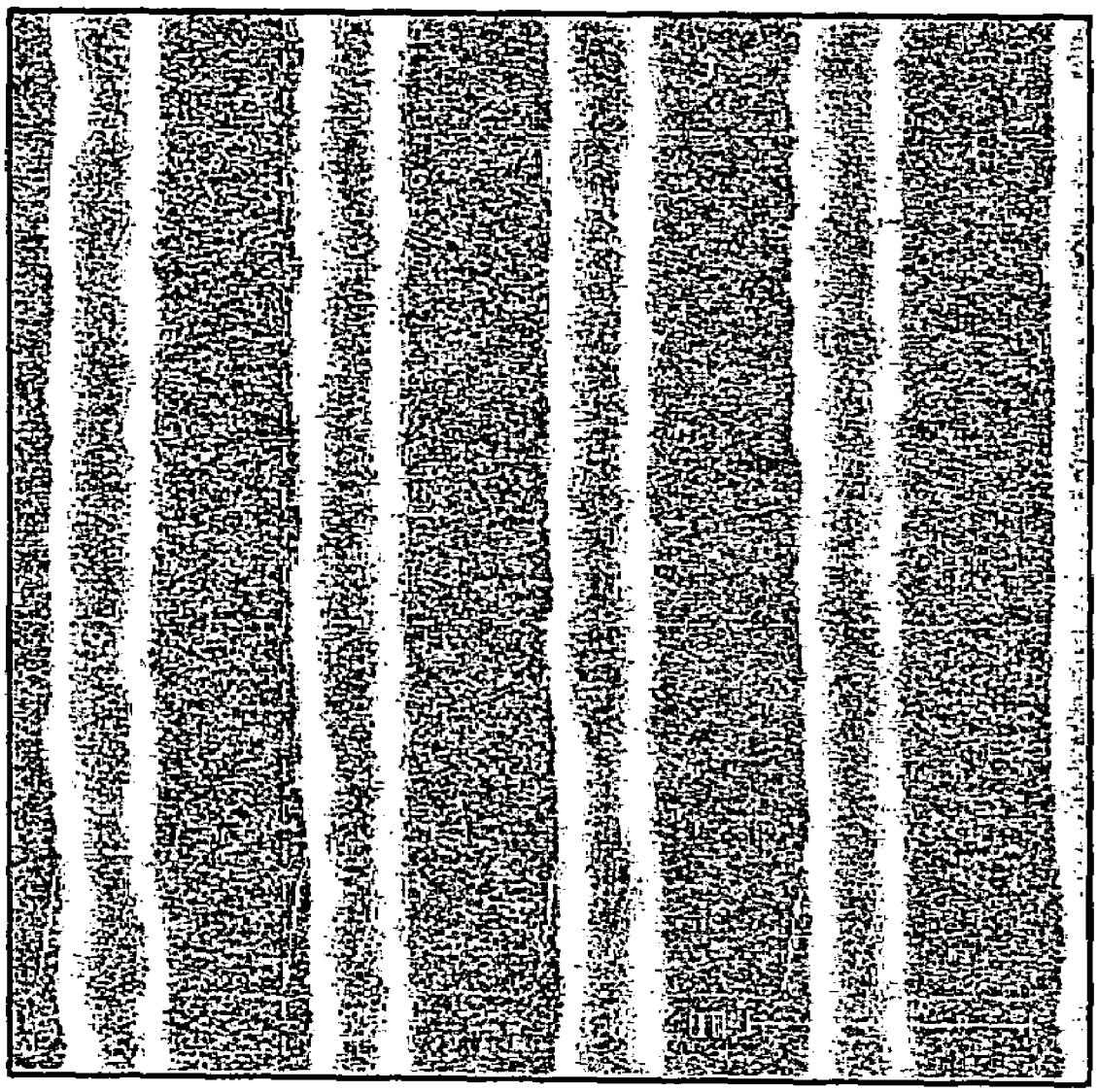
FIG. 3 is a photograph illustrating a photoresist pattern obtained from Example 19.

Photoresist composition was prepared using the same procedure of Example 17 except that 2 g of the polymer obtained from Example 9 was-used instead of the polymer obtained from Example 7, and 0.08 µm of L/S pattern was obtained using said photoresist composition (see FIG. 3).

EXAMPLE 20

Figure 4:
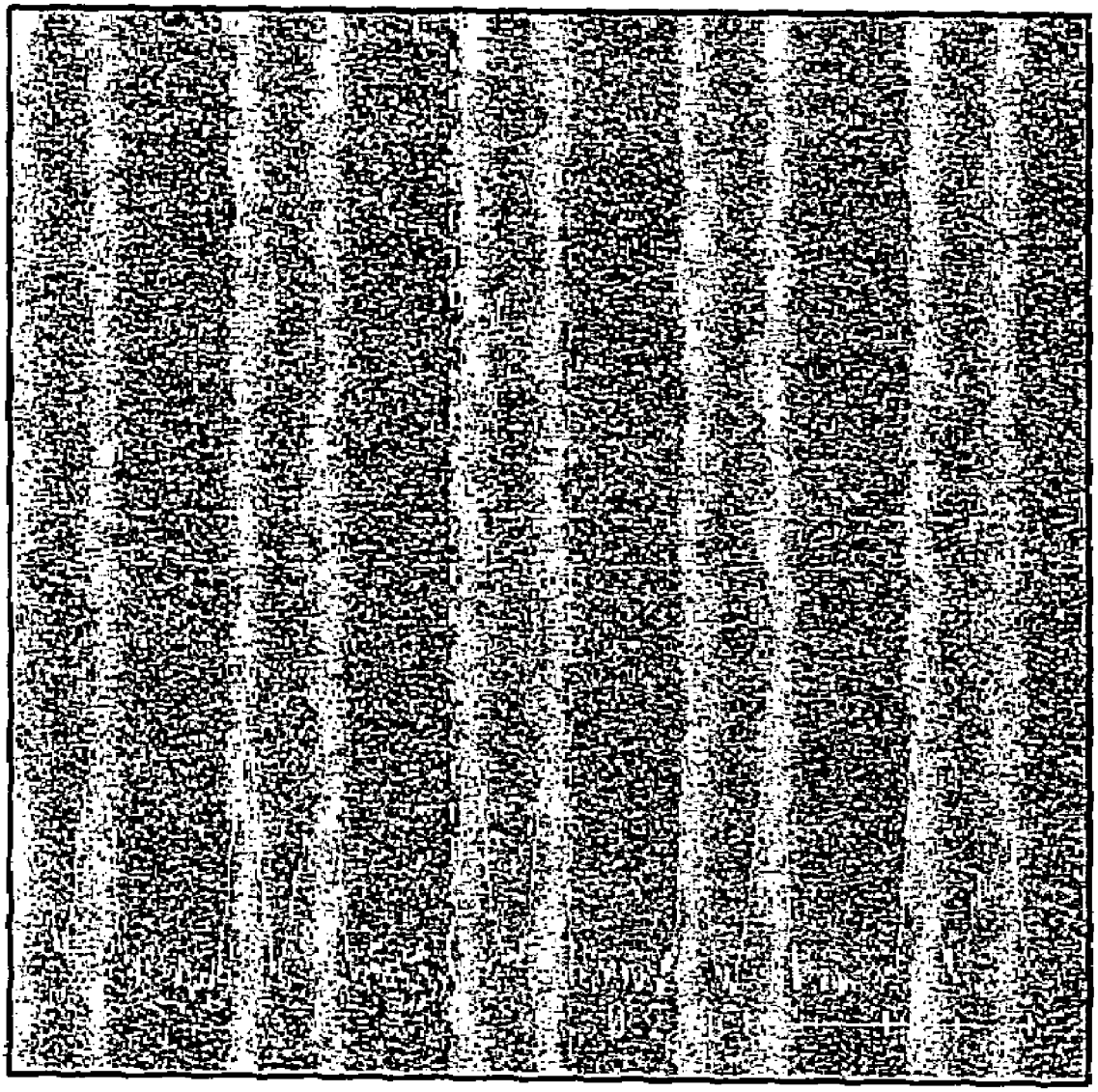
FIG. 4 is a photograph illustrating a photoresist pattern obtained from Example 20.

Photoresist composition was prepared using the same procedure of Example 17 except that 2 g of the polymer obtained from Example 10 was used instead of the polymer obtained from Example 7, and 0.08 µm of L/S pattern was obtained using said photoresist composition (see FIG. 4).

EXAMPLE 21

Figure 5:
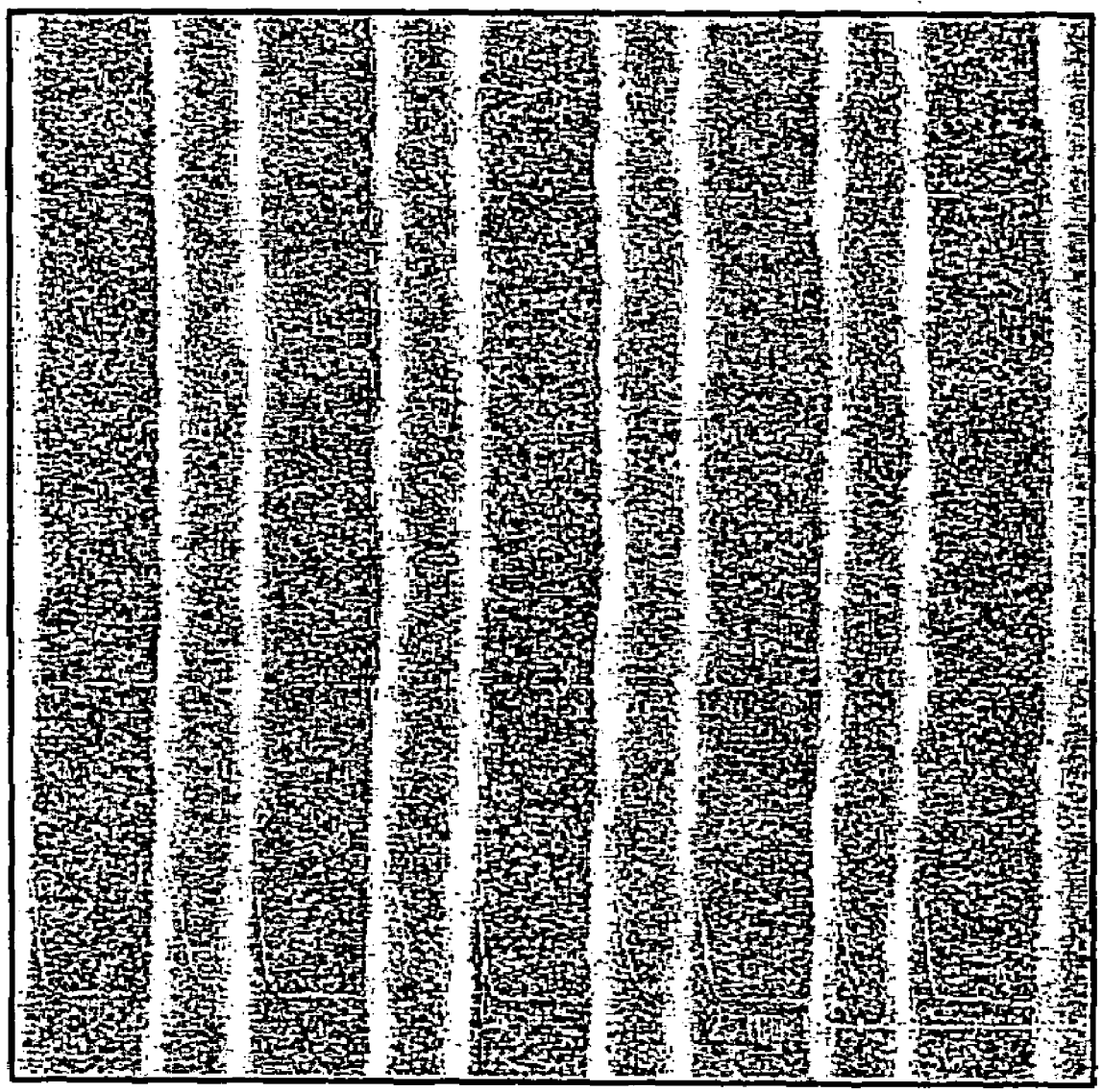
FIG. 5 is a photograph illustrating a photoresist pattern obtained from Example 21.

Photoresist composition was prepared using the same procedure of Example 17 except that 2 g of the polymer obtained from Example 11 was used instead of the polymer obtained from Example 7, and 0.08 µm of L/S pattern was obtained using said photoresist composition (see FIG. 5).

EXAMPLE 22

Figure 6:
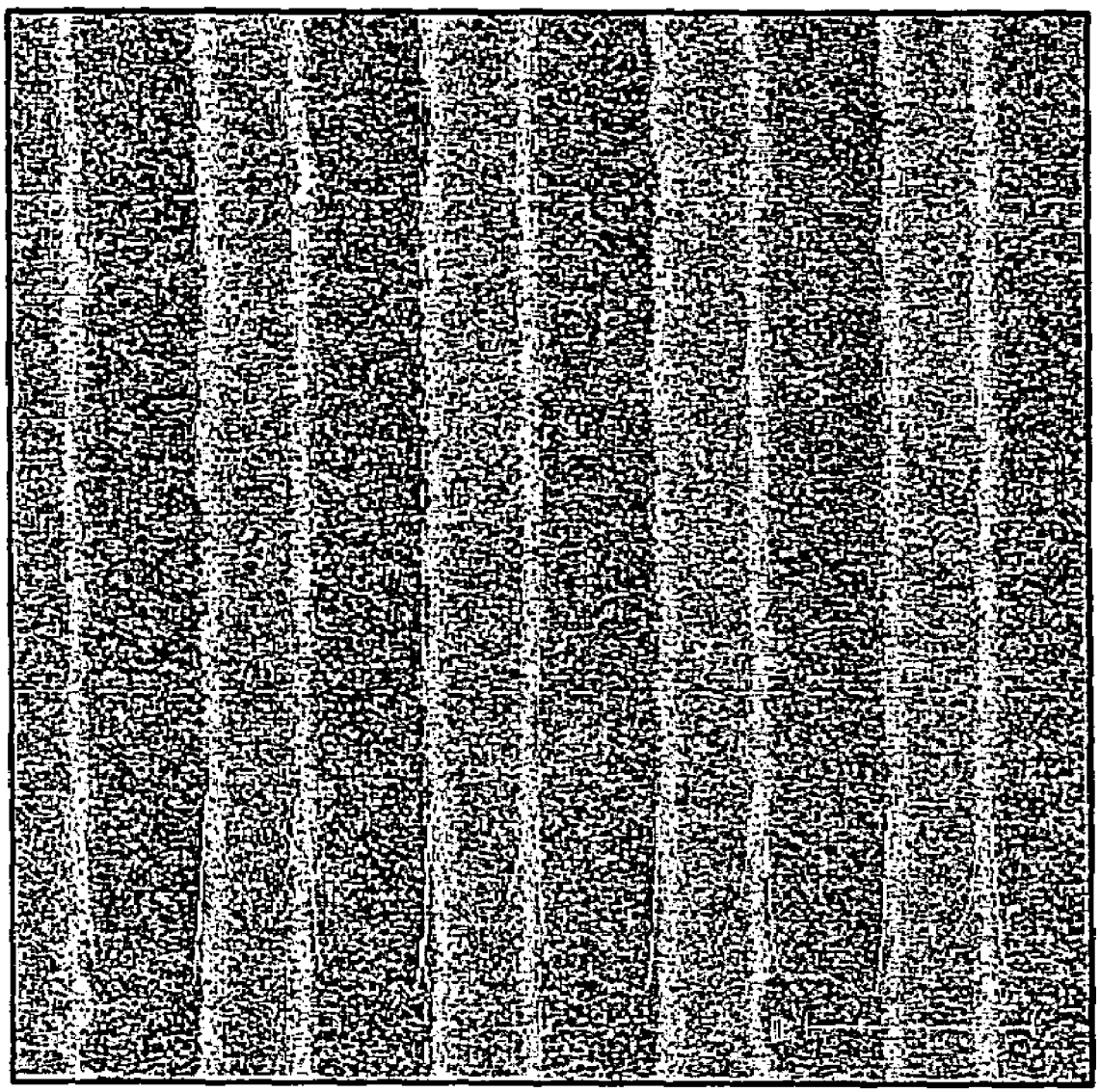
FIG. 6 is a photograph illustrating a photoresist pattern obtained from Example 22.

Photoresist composition was prepared using the same procedure of Example 17 except that 2 g of the polymer obtained from Example 12 was used instead of the polymer obtained from Example 7, and 0.08 µm of L/S pattern was obtained using said photoresist composition (see FIG. 6).

EXAMPLE 23

Figure 7:
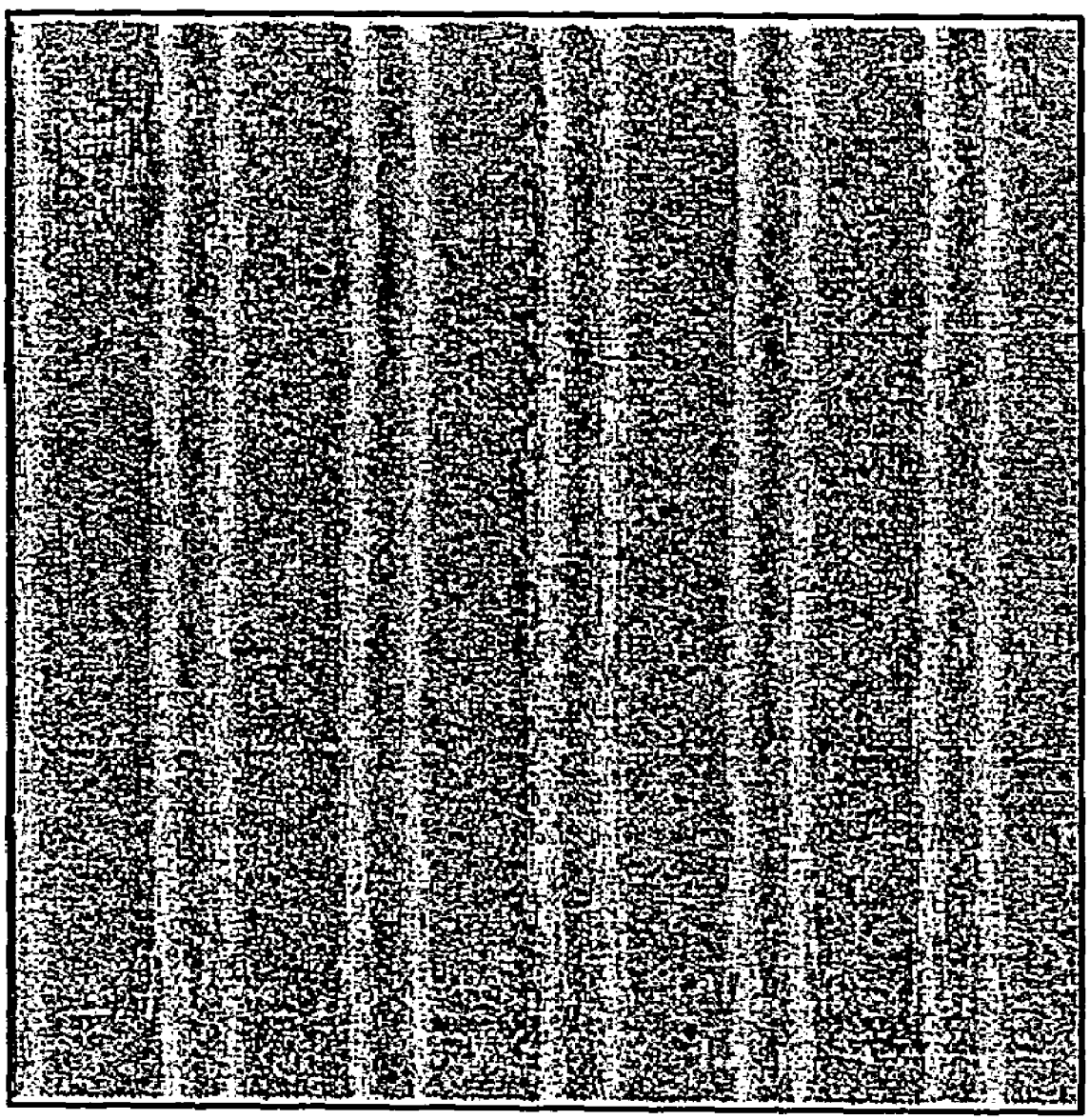
FIG. 7 is a photograph illustrating a photoresist pattern obtained from Example 23.

Photoresist composition was prepared using the same procedure of Example 17 except that 2 g of the polymer obtained from the step (2) of Example 13 was used instead of the polymer obtained from Example 7, and 0.08 µm of L/S pattern was obtained using said photoresist composition (see FIG. 7).

EXAMPLE 24

Figure 8:
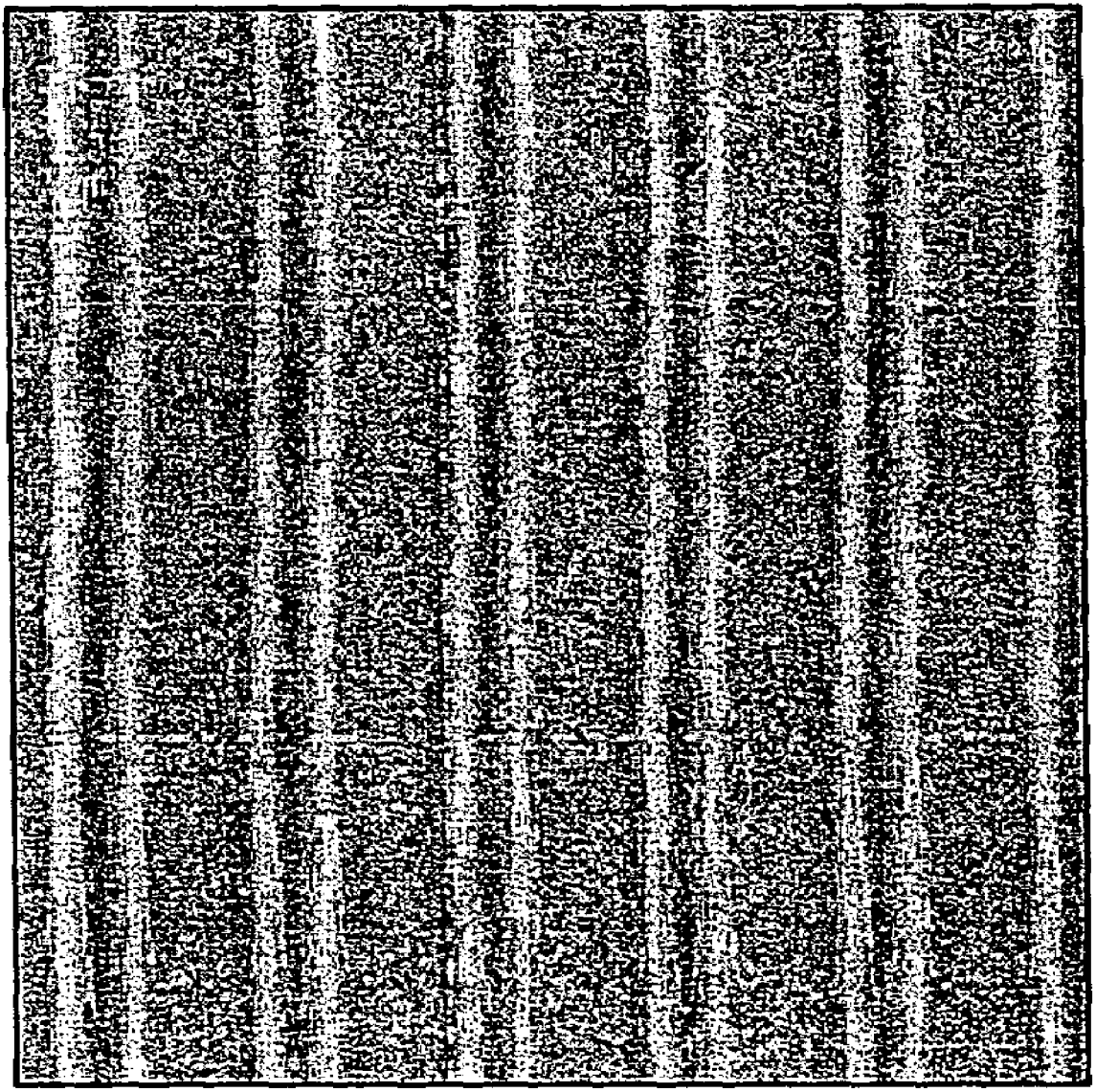
FIG. 8 is a photograph illustrating a photoresist pattern obtained from Example 24.

Photoresist composition was prepared using the same procedure of Example 17 except that 2 g of the polymer obtained from Example 14 was used instead of the polymer obtained from Example 7, and 0.08 µm of L/S pattern was obtained using said photoresist composition (see FIG. 8).

EXAMPLE 25

Figure 9:
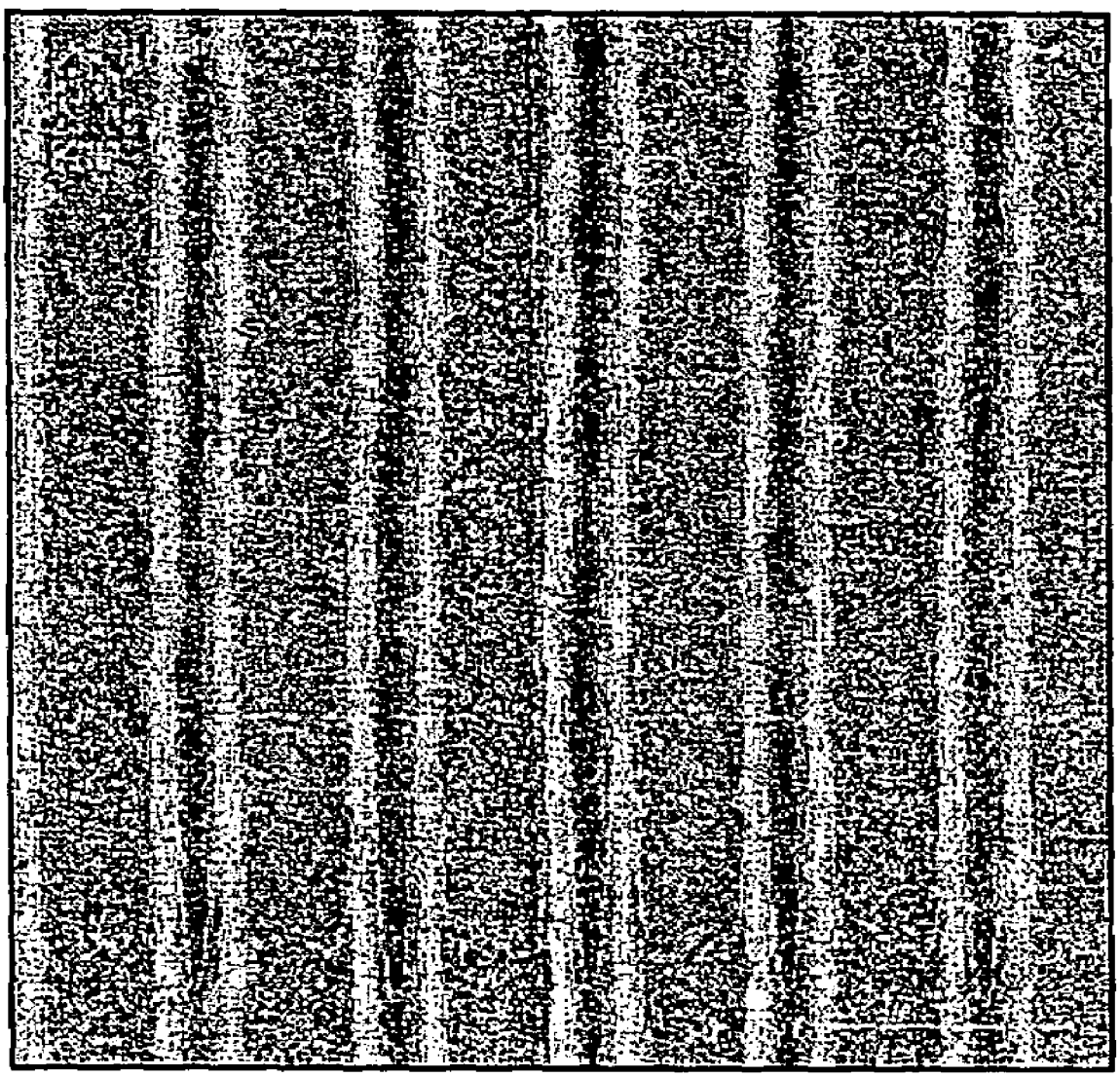
FIG. 9 is a photograph illustrating a photoresist pattern obtained from Example 25.

Photoresist composition was prepared using the same procedure of Example 17 except that 2 g of the polymer obtained from the step (2) of Example 15 was used instead of the polymer obtained from Example 7, and 0.08 µm of L/S pattern was obtained using said photoresist composition (see FIG. 9).

EXAMPLE 26

Figure 10:
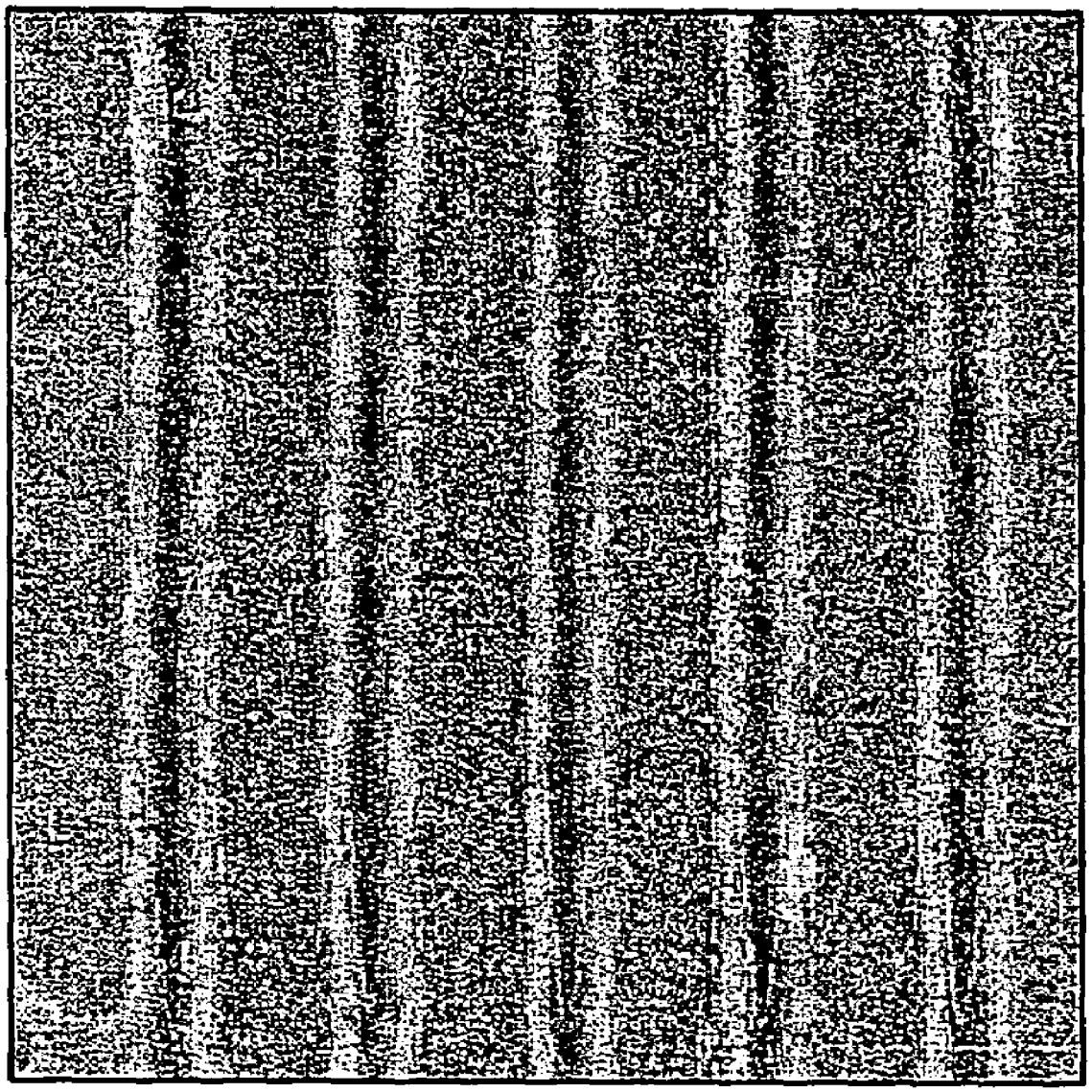
FIG. 10 is a photograph illustrating a photoresist pattern obtained from Example 26.

Photoresist composition was prepared using the same procedure of Example 17 except that 2 g of the polymer obtained from Example 16 was used instead of the polymer obtained from Example 7, and 0.08 µm of L/S pattern was obtained using said photoresist composition (see FIG. 10).

As discussed hereinbefore, patterns having an improved LER can be obtained because the photoresist compositions of the present invention comprising acidic alcohol groups have a high affinity to basic developing solutions. Additionally, the photoresist compositions of the present invention comprising fluorine and sultone have low light absorbance at 193 nm and 157 nm, and do not cause a degassing reaction after exposure in the baking step, thereby preventing damage to the lens. Furthermore, since the photoresist compositions of the present invention have low light absorbance at 193 nm and 157 nm, excellent durability, etching resistance, reproducibility, and resolving power, ultrafine patterns of 4 G, 16 G DRAMs or more as well as of less than 1 G DRAM can be obtained.

What is claimed is:

1. A photoresist polymer comprising a repeating unit represented by Formula 2:

[Formula 2]

(chemical structure showing repeating unit with substituents $R'$, $R''$, $(R)_m$, $R_1$, $R_2$, $R_3$, $R_4$, $R_5$ and a sultone ring with $S(=O)_2$–O)

wherein
  R is $CH_2$, $CHCH_3$, or $C(CH_3)_2$;
  R' and R'' are individually H or $CH_3$;
  $R_1$, $R_2$, $R_3$, $R_4$, and $R_5$ are individually H, F, $C_1$–$C_{20}$ alkyl, $C_1$–$C_{20}$ perfluoroalkyl, $C_1$–$C_{20}$ alkyl comprising an ether group (—O—), $C_1$–$C_{20}$ perfluoroalkyl comprising an ether group (—O—), $C_1$–$C_{20}$ alkyl partially substituted with F, or $C_1$–$C_{20}$ alkyl comprising an ether group and partially substituted with F; and,
  m is an integer ranging from 0 to 3, and k is an integer ranging from 10 to 150.

2. The photoresist polymer according to claim 1, wherein the polymer is selected from the group consisting of Formulas 2a to 2L:

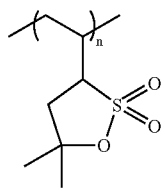

[Formula 2a]

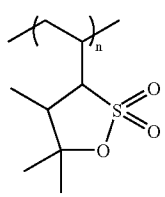

[Formula 2b]

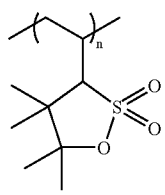

[Formula 2c]

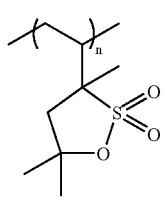

[Formula 2d]

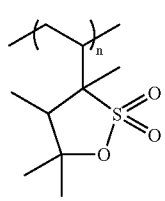

[Formula 2e]

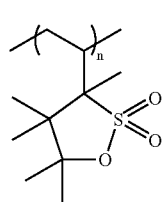

[Formula 2f]

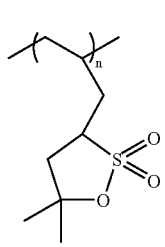

[Formula 2g]

-continued

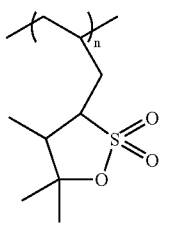

[Formula 2h]

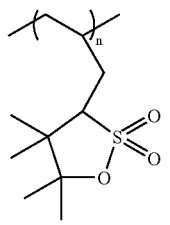

[Formula 2i]

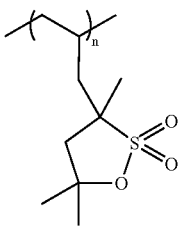

[Formula 2j]

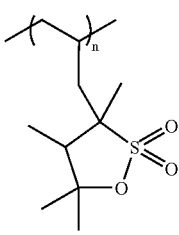

[Formula 2k]

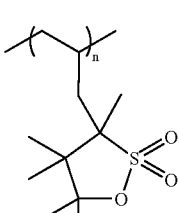

[Formula 2L]

wherein k is an integer ranging from 10 to 150.

3. The photoresist polymer according to claim 1, wherein the polymer comprises a repeating unit of Formula 5:

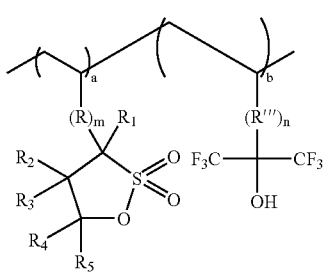

[Formula 5]

wherein

R is CH$_2$, CHCH$_3$, or C(CH$_3$)$_2$;

R''' is C$_1$–C$_5$ alkylene;

R$_1$, R$_2$, R$_3$, R$_4$, and R$_5$ are individually H, F, C$_1$–C$_{20}$ alkyl, C$_1$–C$_{20}$ perfluoroalkyl, C$_1$–C$_{20}$ alkyl comprising an ether group (—O—), C$_1$–C$_{20}$ perfluoroalkyl comprising an ether group (—O—), C$_1$–C$_{20}$ alkyl partially substituted with F, or C$_1$–C$_{20}$ alkyl comprising an ether group and partially substituted with F, and in case that R$_1$, R$_2$ and R$_3$ are all H, then R$_4$ and R$_5$ are not H;

n and m individually are an integer ranging from 0 to 3; and, the relative ratio of a: b=15–99.9 mol %:0.1–85 mol %.

4. The photoresist polymer according to claim 3, wherein the polymer is selected from the group consisting of Formulas 5a to 5x:

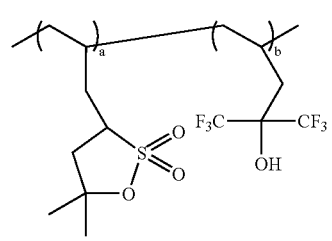

[Formula 5a]

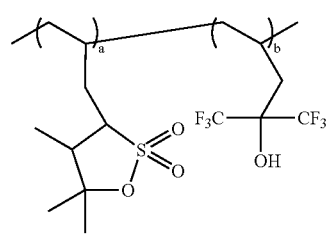

[Formula 5b]

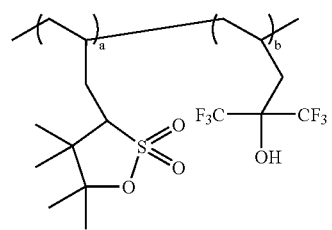

[Formula 5c]

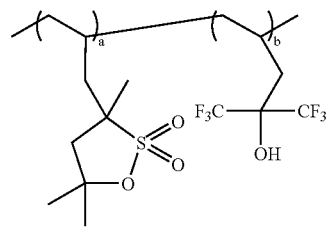

[Formula 5d]

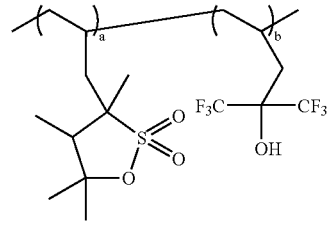

[Formula 5e]

-continued

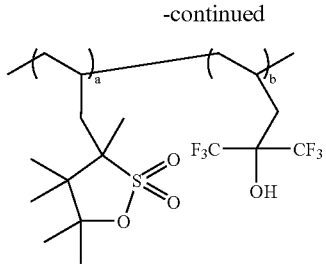

[Formula 5f]

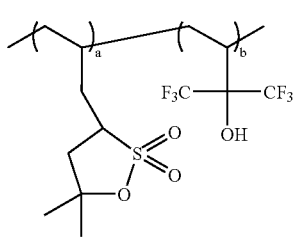

[Formula 5g]

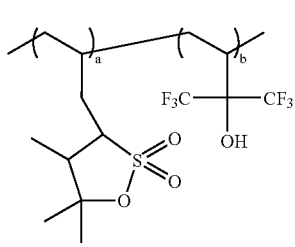

[Formula 5h]

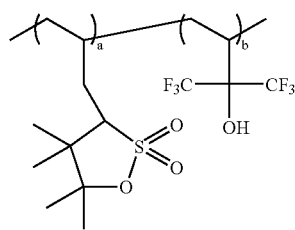

[Formula 5i]

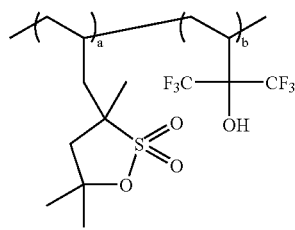

[Formula 5j]

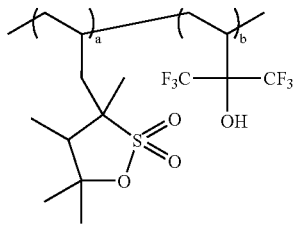

[Formula 5k]

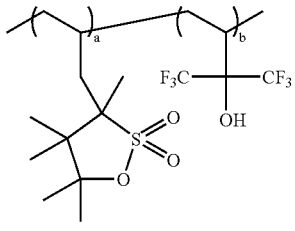

[Formula 5L]

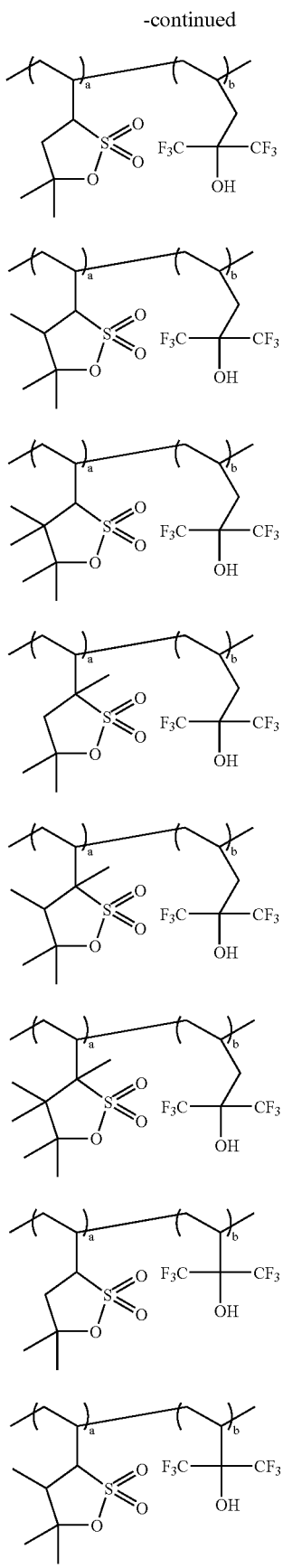
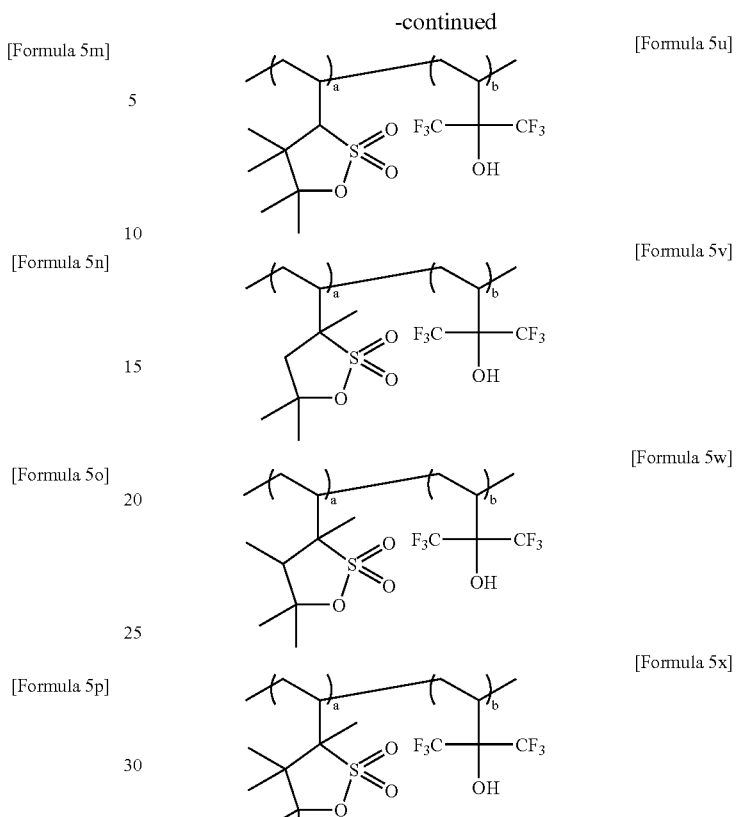

wherein the relative ratio of a: b=15–99.9 mol %: 0.1–85 mol %.

5. The photoresist polymer according to claim 3, wherein the repeating unit of Formula 5 is present in a ratio of 10–95 mol %:90–5 mol % relative to total molar percentage of the polymer.

6. A photoresist composition comprising a photoresist polymer of claim 3, a photoacid generator, and an organic solvent.

7. The photoresist composition according to claim 6, wherein the photoacid generator is selected from the group consisting of phthalimidotrifluoromethane sulfonate, dinitrobenzyltosylate, n-decyl disulfone, and naphthylimido trifluoromethane sulfonate.

8. The photoresist composition according to claim 7, wherein the photoacid generator further comprises any one selected from the group consisting of diphenyl iodide hexafluorophosphate, diphenyl iodide hexafluoroarsenate, diphenyl iodide hexafluoroantimonate, diphenyl p-methoxyphenylsulfonium triflate, diphenyl p-toluenylsulfonium triflate, diphenyl p-isobutylphenylsulfonium triflate, triphenylsulfonium hexafluororarsenate, triphenylsulfonium hexafluoro-antimonate, triphenylsulfonium triflate, and dibutyl-naphthylsulfonium triflate.

9. The photoresist composition according to claim 6, wherein the photoacid generator is present in an amount ranging from 0.05 wt % to 10 wt % based on the weight of the photoresist polymer.

10. The photoresist composition according to claim 6, wherein the organic solvent is selected from the group consisting of diothylene glycol diethyl ether, methyl 3-methoxypropionate, ethyl 3-ethoxypropionate, propylene glycol methyl ether acetate, cyclohexanone, n-heptanone, and ethyl lactate.

11. The photoresist composition according to claim 6, wherein the organic solvent is present in an amount ranging from 500 wt % to 2000 wt % based on the weight of the photoresist polymer.

12. A method for forming a photoresist pattern, comprising the steps of:
(a) coating the photoresist composition of claim 6 on a top portion of an underlying layer to be etched to form a photoresist film;
(b) exposing the photoresist film to light;
(c) baking the exposed photoresist film; and,
(d) developing the photoresist film to obtain a photoresist pattern.

13. The method according to claim 12, further comprising additional baking step before the exposing step (b).

14. The method according to claim 13 wherein the baking step is performed at a temperature ranging from 70° C. to 200° C.

15. The method according. to claim 12 wherein the baking step is performed at a temperature ranging from 70° C to 200° C.

16. The method according to claim 12, wherein the exposing step is performed using a light source selected from the group consisting of KrF, ArF, EUV (Extreme Ultra Violet), VUV (Vacuum Ultra Violet), E-beam, X-ray, and ion beam.

17. The method according to claim 12, wherein the exposing step is performed with exposure energy ranging from 0.1 mJ/cm$^2$ to 100 mJ/cm$^2$.

18. The method according to claim 12, wherein the developing step (d) is performed using an alkaline developing solution.

19. A photoresist composition comprising a photoresist polymer of claim 3, a photoacid generator, and an organic solvent.

20. The photoresist composition according to claim 19, wherein the photoacid generator is selected from the group consisting of phthalimidotrifluoromethane sulfonate, dinitrobenzyltosylate, n-decyl disulfone, and naphthylimido trifluoromethane sulfonate.

21. The photoresist composition according to claim 20, wherein the photoacid generator further comprises any one selected from the group consisting of diphenyl iodide hexafluorophosphate, diphenyl iodide hexafluoroarsenate, diphenyl iodide hexafluoroantimonate, diphenyl p-methoxyphenylsulfonium triflate, diphenyl p-toluenylsulfonium triflate, diphenyl p-isobutylphenylsulfonium triflate, triphenylsulfonium hexafluororarsenate, triphenylsulfonium hexafluoro-antimonate, triphenylsulfonium triflate, and dibutyl-naphthylsulfonium triflate.

22. A method for forming a photoresist pattern, comprising the steps of:
(a) coating the photoresist composition of claim 19 on a top portion of an underlying layer to be etched to form a photoresist film;
(b) exposing the photoresist film to light;
(c) baking the exposed photoresist film; and,
(d) developing the photoresist film to obtain a photoresist pattern.

23. The method according to claim 22, further comprising additional baking step before the exposing step (b).

24. The method according to claim 23 wherein the baking step is performed at a temperature ranging from 70° C. to 200° C.

25. The method according to claim 22 wherein the baking step is performed at a temperature ranging from 70° C. to 200° C.

26. The method according to claim 22, wherein the exposing step is performed using a light source selected from the group consisting of KrF, ArF, EUV (Extreme Ultra Violet), VUV (Vacuum Ultra Violet), E-beam. X-ray, and ion beam.

27. The method according to claim 22, wherein the exposing step is performed with exposure energy ranging from 0.1 mJ/cm$^2$ to 100 mJ/cm$^2$.

28. The method according to claim 22, wherein the developing step (d) is performed using an alkaline developing solution.

29. The photoresist composition according to claim 19, wherein the photoacid generator is present in an amount ranging from 0.05 wt % to 10 wt % based on the weight of the photoresist polymer.

30. The photoresist composition according to claim 19, wherein the organic solvent is selected from the group consisting of diethylene glycol diethyl ether, methyl 3-methoxypropionate, ethyl 3-ethoxypropionate, propylene glycol methyl ether acetate, cyclohexanone, n-heptanone, and ethyl lactate.

31. The photoresist composition according to claim 19, wherein the organic solvent is present in an amount ranging from 500 wt % to 2000 wt % based on the weight of the photoresist polymer.

32. A method for forming the photoresist polymer of claim 1, comprising the steps of:
(a) reacting compounds of Formulas 3 and 4 in the presence of a salt to obtain a compound of Formula 1; and
(b) polymerizing the compound of Formula 1 in the presence of a polymerizing initiator to form a polymer of Formula 2:

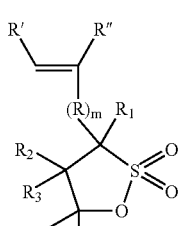

[Formula 1]

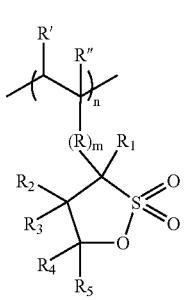

[Formula 2]

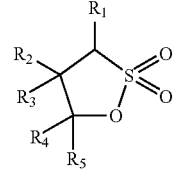

[Formula 3]

-continued

[Formula 4]

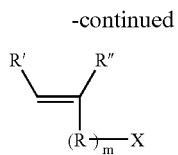

wherein
R is $CH_2$, $CHCH_3$, or $C(CH_3)_2$;
R' and R" are individually H or $CH_3$;
$R_1$, $R_2$, $R_3$, $R_4$, and $R_5$ are individually H, F, $C_1$–$C_{20}$ alkyl, $C_1$–$C_{20}$ perfluoroalkyl, $C_1$–$C_{20}$ alkyl comprising an ether group (—O—), $C_1$–$C_{20}$ perfluoroalkyl comprising an ether group (—O—), $C_{–C20}$ alkyl partially substituted with F or $C_1$–$C_{20}$ alkyl comprising an ether group, and partially substituted with F;
X is F, Cl, or Br; and,
m is an integer ranging from 0 to 3, and k is an integer ranging from 10 to 150.

33. The method according to claim 32 wherein the salt used in step (a) is selected from the group consisting of NaH, n-BuLi, Lithium diisoproylamine (LDA), and LiH.

34. The method according to claim 32 wherein the polymerization reaction of the step (b) is performed using a solvent selected from the group consisting of cyclohexanone, cyclopentanone, tetrahydrofuran, dimethylformamide, dimethylsulfoxide, dioxane, methylethylketone, benzene, toluene, xylene, and mixtures thereof.

35. The method according to claim 32 wherein the polymerization initiator used in the step (b) is selected from the group consisting of selected from the group consisting of benzoylperoxide, 2,2'-azobisiso-butyronitrile (AIBN), acetylperoxide, laurylperoxide, t-butylperacetate. t-butylhydroperoxide, and di-t-butylperoxide.

36. The method according to claim 32 wherein the polymer is crystallized and purified using a solvent selected from the group consisting of dimethylether, petroleum ether, a lower alcohol, water, and mixtures thereof.

37. The method according to claim 36, wherein the lower alcohol is selected from the group consisting of methanol, ethanol, iso-propanol, and mixtures thereof.

38. A method for forming the photoresist polymer of claim 3, comprising the steps of:
(a) reacting compounds of Formulas 7 and 8 in the presence of a salt to obtain a compound of Formula 4; and,
(b) polymerizing compounds 9 and 10 in the presence of a polymerization initiator to form a polymer of Formula 5:

[Formula 7]

[Formula 8]

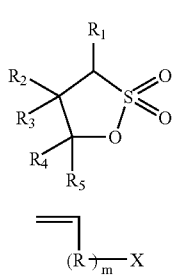

[Formula 9]

[Formula 10]

[Formula 5]

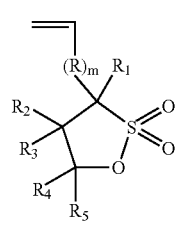

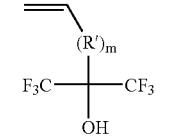

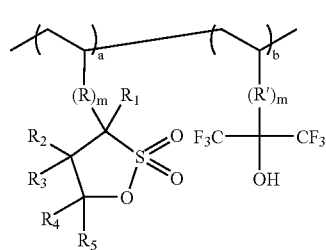

wherein
R is $CH_2$, $CHCH_3$ or $C(CH_3)_2$;
R''' is $C_1$–$C_5$ alkylene;
$R_1$, $R_2$, $R_3$, $R_4$, and $R_5$ are individually H, F, $C_1$–$C_{20}$ alkyl, $C_1$–$C_{20}$ perfluoroalkyl, $C_1$–$C_{20}$ alkyl comprising an ether group (—O—), $C_1$–$C_{20}$ perfluoroalkyl comprising an ether group (—O—), $C_1$–$C_{20}$ alkyl partially substituted with F, or $C_1$–$C_{20}$ alkyl comprising an ether group and partially substituted with F, with the proviso that if $R_1$, $R_2$ and $R_3$ are all H, then $R_4$ and $R_5$ are different from H;
X is F, Cl, or Br, and n and in individually are an integer ranging from 0 to 3; and,
the relative ratio of a: b=15–99.9 mol %:0.1–85 mol %.

39. The method according to claim 38 wherein the salt used in step (a) is selected from the group consisting of NaH, n-BuLi, Lithium diisoproylamine (LDA), and LiH.

40. The method according to claim 38 wherein the polymerization reaction of the step (b) is performed using a solvent selected from the group consisting of cyclohexanone, cyclopentanone, tetrahydrofuran, dimethylformamide, dimethylsulfoxide, dioxane, methylethylketone, benzene, toluene, xylene, and mixtures thereof.

41. The method according to claim 38 wherein the polymerization initiator used in the step (b) is selected from the group consisting of selected from the group consisting of benzoylperoxide, 2,2'-azobisiso-butyronitrile (AIBN), acetylperoxide, laurylperoxide, t-butylperacetate, t-butylhydroperoxide, and di-t-butylperoxide.

42. The method according to claim 38 wherein the polymer is crystallized and purified using a solvent selected from the group consisting of dimethylether, petroleum ether, a lower alcohol, water, and mixtures thereof.

43. The method according to claim 42, wherein the lower alcohol is selected from the group consisting of methanol, ethanol, iso-propanol, and mixtures thereof.

* * * * *